US011010877B2

(12) United States Patent
Ganesan et al.

(10) Patent No.: US 11,010,877 B2
(45) Date of Patent: May 18, 2021

(54) APPARATUS, SYSTEM AND METHOD FOR DYNAMIC IN-LINE SPECTRUM COMPENSATION OF AN IMAGE

(71) Applicant: Canon U.S.A., Inc., Melville, NY (US)

(72) Inventors: Santosh Ganesan, Cambridge, MA (US); Zhuo Wang, Santa Clara, CA (US)

(73) Assignee: Canon U.S.A., Inc., Melville, NY (US)

(*) Notice: Subject to any disclaimer, the term of this patent is extended or adjusted under 35 U.S.C. 154(b) by 419 days.

(21) Appl. No.: 15/881,404

(22) Filed: Jan. 26, 2018

(65) Prior Publication Data
US 2018/0218482 A1 Aug. 2, 2018

Related U.S. Application Data

(60) Provisional application No. 62/451,452, filed on Jan. 27, 2017.

(51) Int. Cl.
*G06T 5/00* (2006.01)
*G06T 5/40* (2006.01)
(Continued)

(52) U.S. Cl.
CPC .......... *G06T 5/009* (2013.01); *A61B 1/00009* (2013.01); *A61B 5/0075* (2013.01);
(Continued)

(58) Field of Classification Search
CPC . A61B 1/00009; A61B 5/0075; A61B 5/0084; A61B 2576/00; G06T 3/4084;
(Continued)

(56) References Cited

U.S. PATENT DOCUMENTS 4,517,589 A * 5/1985 Baba ............... H04N 1/488
358/505
6,844,881 B1 1/2005 Chen et al.
(Continued)

FOREIGN PATENT DOCUMENTS

EP   0 908 849 A1   4/1999
EP   2415390 A1   2/2012
(Continued)

OTHER PUBLICATIONS

Zeidan, A., et al, "Spectral imaging using forward-viewing spectrally encoded endoscopy", Biomedical Optics Express, Feb. 1, 2016, pp. 392-398, vol. 7, No. 2.
(Continued)

*Primary Examiner* — Mekonen T Bekele
(74) *Attorney, Agent, or Firm* — Canon U.S.A., Inc. I.P. Division

(57) ABSTRACT

An image processing apparatus is provided and includes one or more processors and a memory storing instructions. The one or more processors are controlled to receive image stream data captured by an image capturing apparatus and store, in memory, a current image frame from the received image stream data and store, in memory, a previously received image frame from the received image stream data. The previously received image frame having been received at a time earlier than the current image data frame. Using the previously received image frame data stored in memory, a compensation value representing an illumination spectrum of the previously stored image frame data is calculated and image correction is performed on the current image frame data using the calculated compensation value. The corrected current image frame for display on a display device.

40 Claims, 12 Drawing Sheets

(51) Int. Cl.
| | |
|---|---|
| *G06T 3/40* | (2006.01) |
| *G06T 7/10* | (2017.01) |
| *G06T 5/20* | (2006.01) |
| *G06T 7/00* | (2017.01) |
| *A61B 1/00* | (2006.01) |
| *G06T 5/50* | (2006.01) |
| *H04N 5/235* | (2006.01) |
| *A61B 5/00* | (2006.01) |

(52) U.S. Cl.
CPC .......... *A61B 5/0084* (2013.01); *G06T 3/4084* (2013.01); *G06T 5/002* (2013.01); *G06T 5/20* (2013.01); *G06T 5/40* (2013.01); *G06T 5/50* (2013.01); *G06T 7/0012* (2013.01); *G06T 7/10* (2017.01); *H04N 5/2351* (2013.01); *A61B 2576/00* (2013.01); *G06T 2207/10024* (2013.01); *G06T 2207/10068* (2013.01); *G06T 2207/20032* (2013.01)

(58) Field of Classification Search
CPC .......... G06T 5/002; G06T 5/009; G06T 5/20; G06T 5/40; G06T 5/50; G06T 7/0012; G06T 7/10; G06T 2207/10024; G06T 2207/10068; G06T 2207/20032; H04N 5/2351
See application file for complete search history.

(56) References Cited

U.S. PATENT DOCUMENTS

| | | | |
|---|---|---|---|
| 8,928,889 B2 | 1/2015 | Tearney et al. | |
| 9,113,114 B2* | 8/2015 | Lee | H04N 5/2352 |
| 9,224,363 B2 | 12/2015 | Ballestad et al. | |
| 9,254,089 B2 | 2/2016 | Tearney et al. | |
| 9,846,940 B1 | 12/2017 | Wang | |
| 10,694,129 B2* | 6/2020 | Cote | H04N 5/232939 |
| 2004/0222987 A1 | 11/2004 | Chang et al. | |
| 2006/0017720 A1 | 1/2006 | Li | |
| 2006/0054783 A1 | 3/2006 | Voronov et al. | |
| 2006/0268138 A1* | 11/2006 | Higashitsutsumi | H04N 5/23277 348/294 |
| 2007/0146502 A1* | 6/2007 | Ahn | H04N 5/243 348/229.1 |
| 2008/0007692 A1* | 1/2008 | Mihashi | A61B 3/10 351/206 |
| 2008/0298685 A1* | 12/2008 | Maeda | G06T 5/40 382/195 |
| 2011/0150329 A1* | 6/2011 | Lepine | G06T 3/4038 382/165 |
| 2012/0101374 A1 | 4/2012 | Tearney et al. | |
| 2012/0190928 A1 | 7/2012 | Boudoux | |
| 2013/0093867 A1 | 4/2013 | Schick | |
| 2013/0188009 A1* | 7/2013 | Wagatsuma | A61B 6/025 348/36 |
| 2013/0239057 A1* | 9/2013 | Ubillos | G06F 3/04842 715/833 |
| 2014/0218567 A1* | 8/2014 | Han | H04N 5/347 348/239 |
| 2015/0002464 A1* | 1/2015 | Nishioka | G06F 3/0412 345/174 |
| 2019/0323948 A1* | 10/2019 | Leroux | G01N 21/25 |

FOREIGN PATENT DOCUMENTS

| | | |
|---|---|---|
| JP | 2008304541 A1 | 12/2008 |
| WO | 02/38040 A2 | 5/2002 |
| WO | 2015/116939 A1 | 8/2015 |

OTHER PUBLICATIONS

Zeidan, A., et al, "Miniature forward-viewing spectrally encoded endoscopic probe", Optics Letters, Aug. 15, 2014, pp. 4871-4874, vol. 39, No. 16.

Park, H., et al., "Forward imaging OCT endoscopic catheter based on MEMS lens scanning", Optics Letters, Jul. 1, 2012, vol. 37, No. 13.

Kang, D., et al., "Spectrally-encoded color imaging", Optics Express, Aug. 17, 2009, pp. 15239-15247, vol. 17, No. 17.

Penne, J. et al., "Time-of-Flight 3-D Endoscopy", 12th International Conference, London, UK, Sep. 20-24, 2009, pp. 467-474, vol. 5761.

* cited by examiner

APPARATUS, SYSTEM AND METHOD FOR DYNAMIC IN-LINE SPECTRUM COMPENSATION OF AN IMAGE

CROSS-REFERENCE TO RELATED APPLICATIONS

This Nonprovisional patent application claims priority from U.S. Provisional Patent Application Ser. No. 62/451,452 filed on Jan. 27, 2017 which is incorporated herein by reference in its entirety.

This Nonprovisional patent application is related to U.S. Nonprovisional Patent Application Ser. No. 15/830,947 filed on Dec. 4, 2017 which is incorporated herein by reference in its entirety.

BACKGROUND

Field of Art

The present disclosure relates to image processing techniques. More specifically, the disclosure exemplifies techniques for spectrum compensation to be applied to one or more image.

Description of the Related Art

Medical probes have the ability to provide images from inside the patient's body. One useful medical probe employs spectrally encoded endoscopy ("SEE") technology, which is a miniature endoscopy technology that can conduct high-definition imaging through a sub-mm diameter probe. SEE uses wavelength to encode spatial information of a sample, thereby allowing high-resolution imaging to be conducted through small diameter endoscopic probes. SEE can be accomplished using broad bandwidth light input into one or more optical fibers. At the distal end of the fiber, a diffractive or dispersive optical component disperses the light across the sample, which returns back through the optic and then through optical fibers. Light is detected by a wavelength detecting apparatus, such as a spectrometer where each resolvable wavelength corresponds to reflectance from a different point on the sample.

When capturing data reflected from within the human body, the SEE endoscope measures values along a continuous spectrum of light. A drawback associated the captured images manifest itself as a solid dark line or a solid bright line resulting from the emission of light in a narrow frequency range as compared to nearby frequencies. In some instances, due to either background or mechanical noise, or due to the emissive properties of the target, there can be non-uniform bias within this measurement, resulting in distortion. It is thus desirable to correct distortion to improve the image quality.

One such compensation processing technique is an analog technique that counts gray levels in prior frames. The goal of this analog model attempts to address real or near real time processing using minimal image buffers. In this technique, the gray levels of a first frame are counted to obtain a probability distribution of gray levels simultaneously when the first frame is inputted into a source driver of an LCD. A first set of gamma reference voltages is generated according to the probability distribution of gray levels and is supplied to the source driver for the gamma correction for a second frame when the second frame is inputted into the source driver. The loop is repeated when the second frame is input into the source driver and the gray levels of the second frame are counted to obtain a probability distribution of gray levels and to generate a second set of gamma reference voltages for the gamma correction of the third frame. In short, this technique keeps the most recent three or four frames of image data to obtain a distribution of the compensation applied to the most recent frame. The compensation applied to the most recent previous frame is applied to a current frame to determine if a difference between compensation values applied meets a predetermined threshold. If the calculated difference is beneath the threshold, then the compensation value applied to the previous frame is applied to the current frame. However, if the value meets or exceeds the threshold, an entirely new compensation value is calculated for use on the current frame.

A drawback associated with exemplary image correction and normalization techniques relates to the intensity of the calculations needed to derive compensation values. Further, these calculations are not as successful in high frame rate applications such as medical imaging using a SEE endoscope. What is needed is a technique for in-line spectrum image compensation that is usable in a high frame rate environment that overcomes these deficiencies of past systems.

SUMMARY

Accordingly, it can be beneficial to address and/or overcome at least some of the deficiencies indicated herein above, and thus to provide an in-line image compensation algorithm that corrects image data for real-time display thereof.

According to at least one embodiment of the invention, an image processing apparatus is provided and includes one or more processors and a memory storing instructions. The one or more processors are controlled to receive image stream data captured by an image capturing apparatus and store, in memory, a current image frame from the received image stream data and store, in memory, a previously received image frame from the received image stream data. The previously received image frame having been received at a time earlier than the current image data frame. Using the previously received image frame data stored in memory, a compensation value representing an illumination spectrum of the previously stored image frame data is calculated and image correction is performed on the current image frame data using the calculated compensation value. The corrected current image frame for display on a display device.

In one embodiment, the compensation value is calculated by binning and averaging pixel values along a spectral coding direction of the previously received image frame. In another embodiment, the compensation value is calculated by, for each wavelength captured in the previously stored image frame, summing values representative of the wavelength in the spectrally encoded direction and dividing the summed values by a total number of lines of the previously stored image frame.

In one embodiment, image correction on the current image frame is performed by multiplying each pixel value by the calculated compensation value to obtain a corrected pixel value, and generating the corrected image data by storing the corrected pixel values in memory. In another embodiment, image correction on the current image frame is performed using a scaling factor determined based on a maximum brightness value of the previously stored image frame data and for each wavelength value, dividing the maximum brightness value by a brightness value of at each wavelength in the spectrally encoded direction and each pixel of the current image frame data is transformed by the scaling factor to generate the corrected current image frame data. In other embodiments, image correction is performed using the compensation value increases a brightness of pixels having a predetermined darkness level and increases a brightness of pixels having a predetermined brightness level.

In certain embodiments, the current image frame data is stored in a first memory device; and the previously received image frame data is stored in a second different memory device.

In another embodiment, an image processing method is provided. The method receives image stream data captured by an image capturing apparatus, stores, in memory, a current image data frame from the received image stream data and stores, in memory, a previously received image frame from the received image stream data, the previously received image frame having been received at a time earlier than the current image data frame. Using all of the previously received image frame data stored in memory, a compensation value representing an illumination spectrum of the previously stored image frame data is calculated and image correction is performed on the current image frame data using the calculated compensation value. The corrected current image frame is output for display on a display device.

An image processing apparatus comprising one or more processors and a memory storing instructions is provided. The one or more processors are controlled receive image stream data captured by an image capturing apparatus, store, in memory, a current image frame from the received image stream data and store, in memory, a predetermined number of previously received image frames from the received image stream data, each of the predetermined number of previously received image frames having been received at a time earlier than the current image data frame. The predetermined number of previously received image frame data stored in memory is filtered to generate a scaling factor for normalizing pixel brightness. Image correction is performed on the current image frame data using the scaling factor and the corrected current image frame is output for display on a display device.

In one embodiment, the scaling factor is calculated using the predetermined number of previously received image frames by binning and averaging pixel values along a spectral coding direction in each of the predetermined number of previously received image frames and averaging, as a group, the average pixel values for each frame. In another embodiment, the scaling factor is determined is based on a maximum brightness value present in any of the predetermined number of previously stored image frames and for each wavelength value, dividing the maximum brightness value by a brightness value of at each wavelength in the spectrally encoded direction and each pixel of the current image frame data is transformed by the scaling factor to generate the corrected current image frame data.

In another embodiment, the filtering performed on the predetermined number of previously stored image frames is one of (a) a mean filter; (b) a median filter; and (c) an adaptive filter.

In a further embodiment, image correction on the current image frame is performed by multiplying each pixel value by the scaling factor to obtain a corrected pixel value, and the corrected image data is generated by storing the corrected pixel values in memory.

In a further embodiment, at least one region in the predetermined number of previously received image frames is identified as a target region to generate the scaling factor only for pixels within the identified target region and image correction is performed on pixels in a region in the current image frame corresponding to the target region. In another embodiment, pixels in one or more of the predetermined number of previously received image frames are identified as background pixels and image correction is performed on pixels in the current image frame corresponding to pixels identified as background pixels. In other embodiments, one or more pixels in a respective one of the predetermined number of previously received image frames is identified as being indicative of an artifact and excluded from the filtering to generate the scaling factor. In yet another embodiment, the one or more pixels are identified as an artifact by generating a histogram of the respective one of the predetermined number of previously received image frames and selecting pixel values that exceed a predetermined intensity threshold. In other embodiments, the one or more pixels are identified as an artifact by performing binary segmentation on the respective one of the predetermined number of previously received image frames to identify pixels having a brightness value that exceeds a predetermined brightness threshold to generate a map of the identified pixels and exclude the mapped pixels from the filtering.

In further embodiments, a window generated having a predetermined pixel width and predetermined pixel height at an origin point on a respective one of the predetermined number of previously received image frames. The generated window is moved over the respective one of the predetermined number of previously received image frames and kernel smoothing is performed on pixels within the generated window as the generated window is moved to improve signal to noise ratio in the respective one of the predetermined number of previously received image frames.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

Figure 1:
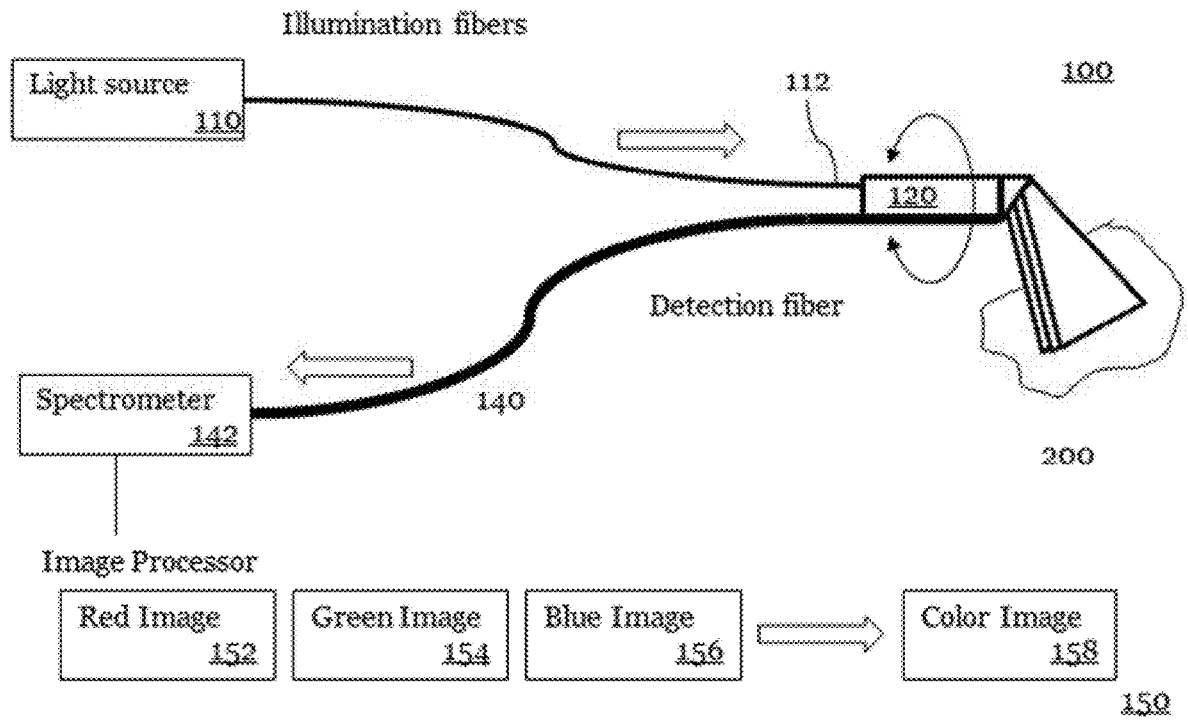
FIG. 1 is a diagram of an embodiment.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION

According to the present disclosure an image processing system and method are provided. The image processing system and method advantageously improves, on a frame-by-frame basis, one or more images that have been captured by an image capturing apparatus for display on display device. The image processing system according to invention principles executes one or more spectral compensation algorithms that are applied in real-time and which dynamically increase a field of view of a target area captured by the image capturing device while minimizing an amount of distortion (e.g. smoothing noise) in the target area. Increasing the field of view without distorting the target area is critically important in medical imaging applications where those charged with reviewing and analyzing image data need to be able to view images of high quality in order to diagnose potential ailments. Further, the spectral compensation algorithms executed by the image processing system make more efficient use of computing resources by improving memory allocation and reducing a number of calculations that need to be performed on a frame-by-frame basis to yield the improved image that will be displayed on a display device.

An exemplary embodiment of an image capturing apparatus that captures a series of moving images is shown in FIG. 1. The image processing apparatus may include any probe or apparatus that is selectively inserted into a body of a subject (e.g. human or animal) in order to obtain an image of a target area within the body of a subject. In one exemplary embodiment, the image processing apparatus may be a SEE probe system 100. This exemplary SEE probe system 100 may include a light source 110, a probe 120, a spectrometer 142, and an image processor 150. In another embodiment, the SEE probe system may include a display device for selectively displaying images captured via the probe 120 and processed by the image processor 150. In another embodiment, the SEE probe system may include one or more storage devices on which captured image data may be stored.

In this embodiment, broadband light from the light source 110 is coupled into a light guiding component which may be an illumination optical fiber 112. The broadband light has sufficient bandwidth to allow for spatial resolution along the spectrally dispersed dimension. In some embodiments, the broadband light is a broadband visible light sources that includes a blue band of light (including wavelength $\lambda_{B1}$ to $\lambda_{BN}$), a green band of light ($\lambda_{G1}$ to $\lambda_{GN}$), and a red band of light ($\lambda_{R1}$ to $\lambda_{RN}$). For example, the blue band contains 400-500 nm light, the green band contains 500-600 nm light, and the red band contains 600-800 nm. In other embodiments, the wavelengths of the broadband light are optimized for identifying specific features such as blood, tissue, etc., and may extend into the near-IR region, for example 1200 nm. In an embodiment, each wavelength band may have wavelength range that is greater than 30 nm. An embodiment may include at least three bands which would allow the SEE to produce color images. More bands may be used to acquire additional information.

The broadband light source 110 may include a plurality of light sources or may be a single light source. The broadband light source 110 may include one or more of a laser, an OLED, a LED, a halogen lamp, an incandescent lamp, supercontinuum light source pumped by a laser, and/or a fluorescent lamp. The broadband light source 110 may be any light source that provides light which can then be split up into at least three bands in which each band is further dispersed to provide light which is then used for spectral encoding of spatial information. The broadband light source 110 may be fiber coupled or may be free space coupled to another component of the SEE probe system 100.

A light guiding component may be an illumination fiber 112 or some other optical waveguide which is connected to an SEE probe 120. The illumination fiber 112 may be a single-mode fiber, multi-mode fiber or double clad fiber. Preferably, a single fiber is used as the illumination fiber 112. The probe 120 or parts thereof may be rotated or oscillated as indicated by the arrow. For example, the illumination fiber and illumination optics may be rotated via a rotary junction.

After illumination of the diffracted light (e.g., red, green, and blue light) on the sample 200 (e.g., a tissue or in vivo sample), light is reflected, scattered, photoluminescence by the sample 200. This light is collected by the detection fiber 140 which may or may not pass through a grating. Detection fiber(s) 140 used to collect the light may be attached on or near the side surface of the a lens of the probe 120. The detection fiber 140 may optionally be rotated along with the illumination optics or may be stationary. If rotated, the detection fiber 140 may be connected, via a rotary junction, to a second non-rotating detection fiber.

As shown in FIG. 1, the collected light is delivered to the spectrometer 142 via the detection fiber 140. The spectrometer 142 obtains 1D spectral data for the 3 wavelength bands (e.g., blue, green, and red light). This 1D spectral data corresponds to information from the three illumination lines (RGB) on sample 200. In certain embodiments, the detection 140 includes a plurality of individual detection fibers arranged in substantially circular pattern in the probe that surrounds the illumination fiber 120. In such an embodiment, each respective detection fiber can detect 1D spectral data for each of the 3 wavelength bands as discussed above.

The probe 120 of FIG. 1 is rotated around the optical axis by a motor as indicated by the arrow such that illumination light lines scan the sample, and 2D data (wavelength and time) may be obtained by the spectrometer 142. The motor can be, for example, a Galvano motor, stepping motor, a piezo-electric motor, or a DC motor. A rotary junction may be used for rotation of the probe. For example, by rotating the spectrally encoded lines in the direction of the arrow, a circular region can be imaged. This circular region can be located approximately perpendicular to the SEE probe, and therefore, the exemplary SEE probe shown in FIG. 1 can conduct forward-view imaging if m and G are chosen so that light is diffracted at angle of $\theta_d = -\theta_i$. Alternatively, the probe 120 may be oscillated to provide similar 2D data. At the spectrometer 142, the wavelength of the collected light can be read out, which can be used to generate a line image of the sample.

After the spectrometer and one or more detectors detects the collected light, an image processor 150 generates three 2D images (152, 154, 156) for red, green, and blue from the data. In other embodiments, two, four, or more 2D images are formed using a probe with appropriate overlapping orders of diffracted light.

The image processor 150 builds a 2D color image 158 from the 3 substantially monochromatic images: a red image 152; a green image 154, and a blue image 156. In certain embodiments where there are a plurality of detection fibers, the building of the 2D color image 158 may be derived from a set of red images, a set of green images and a set of blue images wherein each set is derived from respective ones of the plurality of detection fibers at a given time. This color image 158 may be created so as to simulate a true color image or may be adjusted to highlight differences in, for example, tissue type. In some embodiments, a two or four tone image may be built instead of or in addition to the color image 158. The image processor 150 further executes one or more image correction algorithms on the generated color image 158 as will be discussed below.

In one embodiment, the image processor 150 includes one or more computer unit(s) and one or more display unit(s) which may be connected to the image processor 150 via a high definition multimedia interface (HDMI). The description of an HDMI connection is provided for exemplary purposes only and any other connection interface able to output high definition video image data maybe be used.

Figure 2:
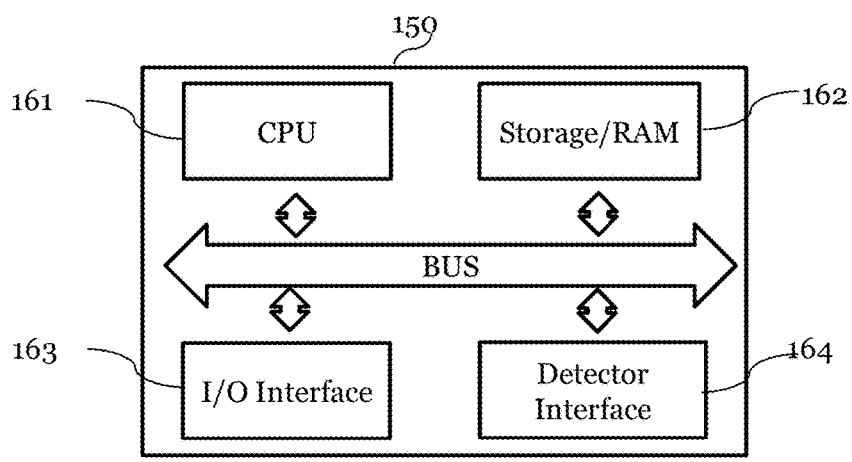
FIG. 2 is a block diagram of an embodiment.

FIG. 2 is an illustration of the hardware components that may comprise the image processor 150 described hereinabove in FIG. 1. The image processor 150 includes one or more processor(s) 161 that execute one or more stored control algorithms. The one or more processor(s) 161 may execute instructions to perform one or more functions for operating the image capture apparatus (a) automatically in response to trigger events, (b) in response to user input or (c) at a predetermined time. The image processor may include an I/O interface in which commands are received via one or more an included or separately attached touch panel screen, keyboard, mouse, joy-stick, ball controller, and/or foot pedal. A user/operator may cause a command to be initiated so as to observe or gather information about a subject which may be inside a human body through an exemplary frontview SEE probe using the image processor 150. For example, when the user inputs a command, the command is transmitted to a CPU 161 for execution thereby.

The image processor 150 may include a CPU 161, Storage/RAM 162, I/O Interface 163 and a Detector Interface 164. Also, the image processor 150 may also comprise one or more devices. The image processor may include one or more general purpose computers or may include application specific processors, such as an ASIC, DSP, FPGA, GPU, FPU, etc.

The image processor 150 may be programmed to execute one or more image processing algorithms such as noise reduction, coordinate distortion correction, contrast enhancement and so on. In one embodiment, the image processor 150 performs spectral compensation in real-time to improve the field of view captured during image capturing operation. After or even during the image processing, the data may be transmitted from the image processor 150 to a display. In some exemplary embodiments, a liquid crystal display may be the display. The display may display, for example, the individual images obtained from a single mode or a composite color image according to various exemplary embodiments of the present disclosure. The display may also display other information than the image, such as the date of observation, what part of the human body is observed, the patient's name, operator's name and so on.

The one or more processors 161 may include a CPU which is configured to read and perform computer-executable instructions stored in the Storage/RAM 162. The computer-executable instructions may include those for the performance of the methods and/or calculations described herein. The Storage/RAM 162 includes one or more non-transitory computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 162 may store computer-readable data and/or computer-executable instructions.

The storage/RAM 162 also includes at least one buffer allowing for the temporary storage of image data captured by the probe 120. In one embodiment, a first buffer stores a predetermined number of frames of image data captured by the probe which have already have been processed by one or more image processing algorithm. In one embodiment, the first buffer stores a series of frames of image data where each of the stored frames has undergone spectral compensation. A second buffer is also provided for temporarily storing the RAW, unprocessed image data representing a current frame that has not yet undergone spectral compensation. The predetermined number of frames of image data stored in the first buffer are used by the spectral compensation algorithm to calculate compensation values that will be applied to the current frame data stored in the second buffer. At the completion of spectral compensation of the current frame, that data is both retrieved by a display processor which displays the compensated data on a display device and also provided to update the first buffer with compensated frame data in order maintain, in the first buffer, the most recent set of frames prior to a current frame.

The I/O interface 163 provides communication interfaces to input and output devices, which may include a keyboard, a display, a mouse, a printing device, a touch screen, a light pen, an optical storage device, a scanner, a microphone, a camera, a drive, communication cable and a network (either wired or wireless). The detector interface 163 also provides communication interfaces to input and output devices. The detector may include a detection system such as the spectrometer 142, components within the spectrometer, for example a photomultiplier tube (PMT), a photodiode, an avalanche photodiode detector (APD), a charge-coupled device (CCD), multi-pixel photon counters (MPPC), or other and also components that provide information about the state of the probe such as a rotary encoder, motor drive voltage, thermocouple, etc. Also, the function of detector may be realized by computer executable instructions (e.g., one or more programs) recorded on a Storage/RAM 162.

In an exemplary operation, the user may place the exemplary SEE probe into a sheath, and then may insert such arrangement/configuration into a body of a subject at a predetermined position thereof. The sheath alone may be inserted into the human body in advance, and it is possible to insert the SEE probe into the sheath after sheath insertion. The exemplary probe may be used to observe inside a human body and works as endoscope such as arthroscopy, bronchoscope, sinuscope, vascular endoscope and so on.

Figure 3:
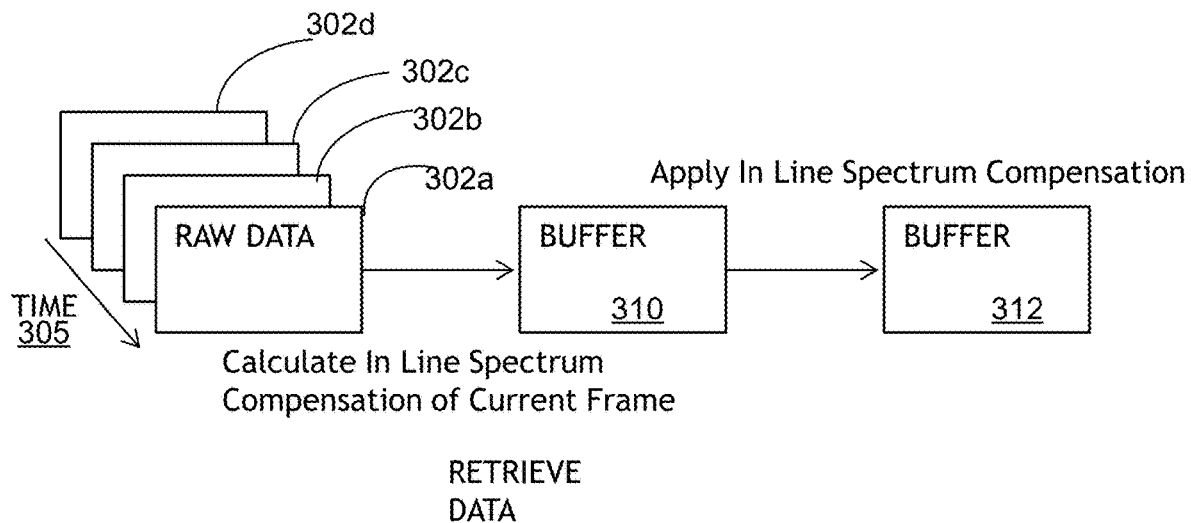
FIG. 3 is a schematic of an embodiment.

FIG. 3 illustrates an exemplary workflow of an image processing algorithm for correcting individual frames of an input data stream captured from the probe 120 of FIG. 1. The image processing algorithm shown in this embodiment is an algorithm for providing in-line spectral compensation in order to advantageously increase a field of view within the captured image frames. As shown in FIG. 3, a series of image frames 302a-302d have been captured by the probe 120 over a period of time represented by the arrow 305. The depiction of four image frames 302a-302d is provided for illustrative purposes only and the number of image frames captured and upon which the image processing algorithm may be applied is limited only by the specification of the probe 120 used to capture the data from the subject. For example, it is expected that the probe 120 may capture image frames at a high frame rate such as 30 Hz or more. As such, a steady stream of image frame data is captured and processed accordingly.

The workflow depicted in FIG. 3 is performed in a frame by frame basis in substantially real-time so that the processed image frame data can be provided for display on a display device allowing a user to view and analyze the image in order to obtain visual feedback resulting in further movement of the probe 120 to capture additional image data from within the subject. The workflow described throughout this description can be applied in real time as the images being captured by the probe 120 are being processed for output in color (e.g. RGB) to a display. In exemplary operation, a process for generating color images representing an imaging surface captured by an image capture apparatus such as the SEE probe system includes obtaining raw (e.g. red channel data, green channel data and blue channel data all stitched together) spectrum data having a predetermined bit size and captured in an array of a predetermined size. The array includes a predetermined number of lines scanned by the probe where each line has a predetermined number of pixels and including a predetermined number of sensors used in capturing the spectral information of each pixel and line. In one embodiment, the array may be one having a dimension of 1000×2048×2, where there are 1000 lines each having 2048 pixels and the information is being captured by 2 sensors. In one embodiment, the two sensors include a first sensor for capturing light wavelength in the red and green band and the second sensor capturing light wavelength in the blue band. This sensor array is described for purposes of example only and any number of sensors can be used. Moreover, it is possible to have dedicated sensor to capture each of the red, green and blue bands. Further it is also possible for there to be more than one sensor used to capture the same spectral band (e.g. 2 sensors to capture wavelengths in the blue spectrum). Upon capturing the raw data, one or more spectrum compensation processes, including the one described hereinbelow, can be performed on the obtained raw data can be performed. Other spectrum compensation processing may include, but is not limited to, correction algorithms that correct for spectral variation of the source power and diffraction efficiency. Scale correction may be performed so that the spectrums are of substantially the same size by adjusting the horizontal dimension of each color channel so that the scaled data of each spectrum can be combined into a single RGB image by overlaying each channel and performing circularization of the rectangular overlay image for display on a display device. In embodiments such as the one described hereinbelow, the algorithms may be adapted to include a loop equal to the number of color spectrums such that the processing steps of the algorithm are performed on each frame in each color spectrum. This advantageously enables spectrum compensation to be performed on per color channel basis so that pixels in the respective color channel can be dynamically corrected prior to circularization of the image data which is output for display on the display device Image frame 302a represents a current frame of RAW, unprocessed image data captured by the probe 120. As used herein, the term image frame is intended to mean a data object that includes a data values representative of individual pixels. For example, if the image captured is a grayscale image, each pixel is represented by an 8-bit integer ranging between 0 and 255 to represent a brightness value of the particular pixel where 0 is black and 255 is white and all other intervening values represent different shades of gray. In a color image, each pixel is defined by separate data values for Red, Green and Blue components. Because of the multicomponent aspect of color images, the pixel value may represent a vector.

In operation, each image frame is generated when the probe 120, which includes a sensor at the base thereof and adjacent the target area being image, senses light that is reflected and refracted from a surface being imaged. In one embodiment, the sensor is a line sensor having one or more divisions each of which is responsible for absorbing a predetermined wavelength of light. Thus, each bit of data is acquired as a line in a particular scanning direction as the probe is rotated about an axis and is stitched together after a predetermined number of lines has been acquired. In one example, a frame represents all of the lines captured after a single 360 degree rotation. In this example, there are 1024 lines per 360 degree rotation. However, this is provided for purposes of example only and the number of lines captured by the sensor per 360 degree rotation may be greater or less than 1024 depending on how fast the probe is rotated and the speed at which the sensor can capture individual lines of data. As the number of lines captured increases, so does the resolution of the images.

The spectrally encoded endoscopic images are obtained by measuring attainable values along a continuous spectrum of light. This spectrum can take the form of a dark or bright line which is otherwise uniform, resulting from the emission of light in a narrow frequency range, compared with nearby frequencies. In some instances, due to either background or mechanical noise, or due to the emissive properties of the target, there can be non-uniform bias within this measurement, resulting in distortion. An in-line spectral compensation algorithm according to the present disclosure can normalize this bias within a frame of line data, in pseudo real time, without regards to background or mechanical noise or target properties.

Figure 4:
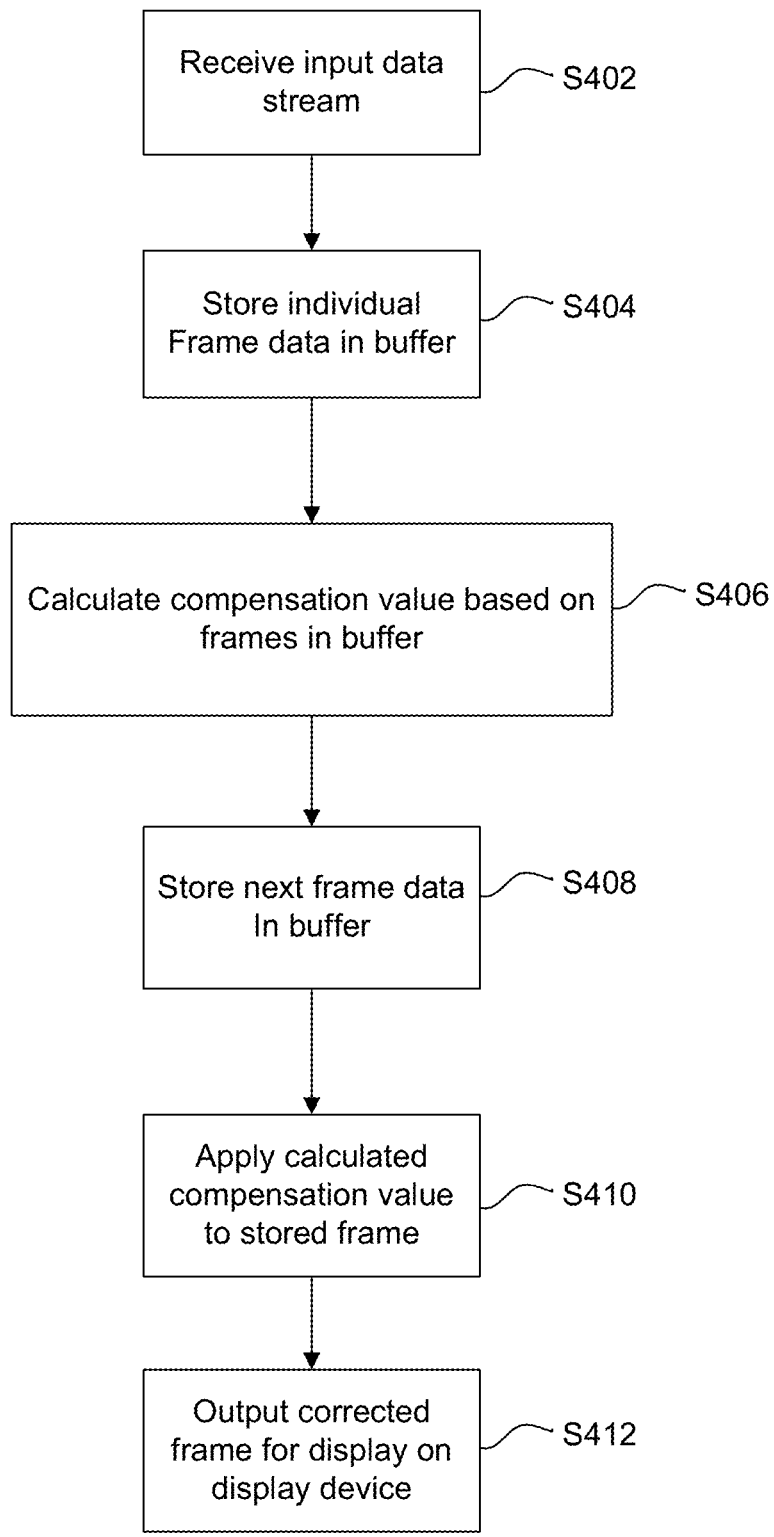
FIG. 4 is a flow diagram of an algorithm of an embodiment.

At a current time (t=0), each current image frame 302a including RAW, unprocessed image data, is stored in a first buffer 310. The in-line spectral compensation algorithm as described in FIG. 4 is applied to the current image frame 302a to obtain an image compensation value to be applied to the current image frame 302a in order to generate a compensated image frame which can then be output for display. The compensation value calculated based on the frame stored in the first buffer 310 is applied to the RAW image frame data stored in a second buffer 312. After performing the in-line spectrum compensation which seeks to brighten the darker pixels in the frame while darkening the brighter pixels in the frame, the compensated (or corrected) image is output for display.

Figure 5:
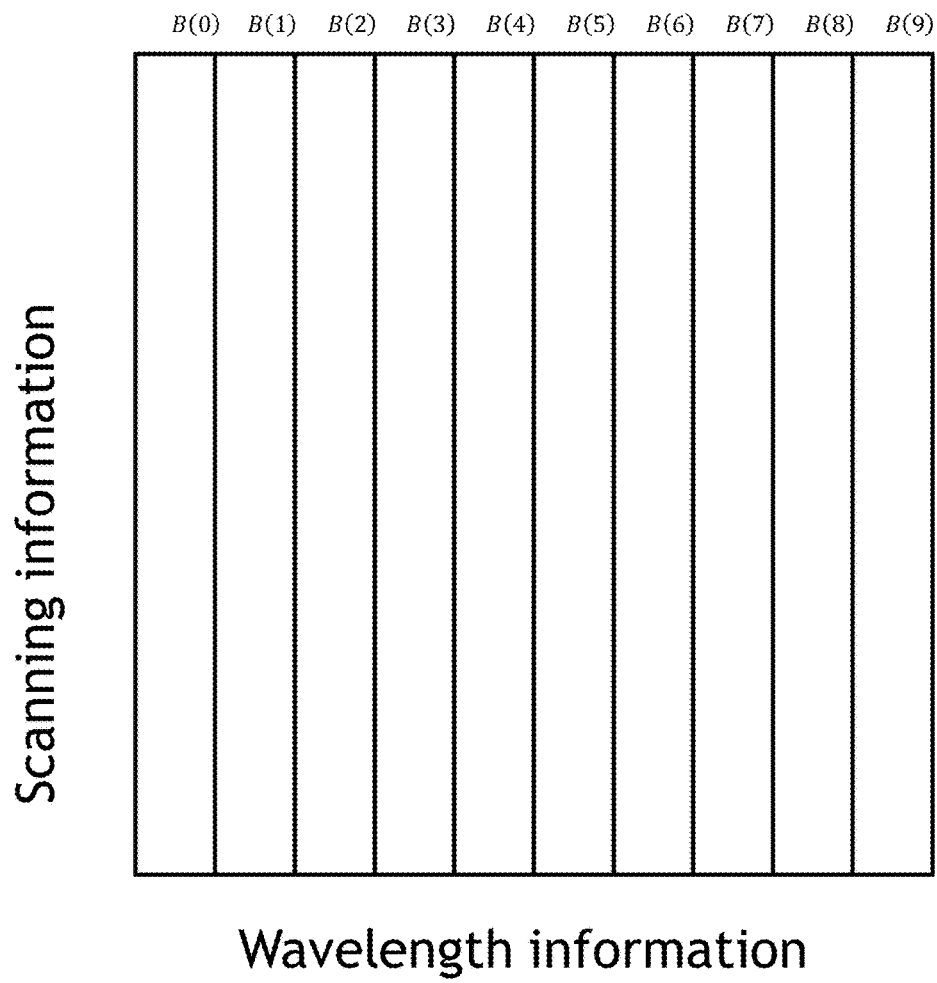
FIG. 5 is a graph of an embodiment.

FIG. 4 illustrates an exemplary embodiment of an in-line spectral compensation algorithm according to principles of this disclosure. Line data is captured by the probe (120 in FIG. 1) is provided to the image processor (150 in FIG. 1) which generates individual data frames at the completion of a single 360 degree rotation of the probe. Each frame of the data stream is received at step S402. A current frame of image data is stored in a buffer in step S404 and, in step S406, a compensation value associated with the stored frame is calculated. In one embodiment, the compensation value is calculated by binning and averaging pixel values along the spectral coding direction as shown in the graph of FIG. 5. FIG. 5 depicts a series of columns representing a predetermined number of wavelengths able to be sensed by the sensor on the probe. The example shown in FIG. 5 depicts nine different sets of wavelengths, B(0)-B(9), that are able to be sensed. The depiction of nine sets of wavelengths is provided for exemplary purposes only and the number of different wavelength groups is dependent on the characteristics of the sensor on the probe. Data for each of these groups of wavelengths are plotted along the x-axis of the graph while information regarding the scanning direction (e.g. number of lines scanned and used to generate the frame) is shown on the y-axis.

In order to calculate a compensation value for the current frame, the algorithm generates a function representing the illumination spectrum including coupling efficiency spectrum for the system. This function takes into account that the light sensed by the probe differs from the light emitted by the light source which may be degraded due to various mechanical components of the system including, but not limited to the efficiency of the connectors which couple the light source to the probe. In other words, each column in FIG. 5 is summed in the spectrally encoded direction and divided by the number of lines that make up the current frame (e.g. 1024) in order to normalize for each wavelength. In one embodiment, the function may be generated in accordance with Equation 1 which states:

$$B(x) = \frac{\sum_{k=1}^{n} A(x, k)}{n} \quad (1)$$

This function is calculated by taking the RAW data for each frame A(x,y) where x is the index for the spectrally encoded direction and y is the index for the scanning direction. Thus, B(x) represents the illumination spectrum including coupling efficiency and for each set of wavelengths (B(0)-B(9) in FIG. 5), a sum of wavelength values at each line is taken and that sum is divided by the number of lines n of the current frame. While B(0)-B(9) are used in this exemplary embodiment, the number of columns B depending the definition of the image capture device and the amount of data the camera can see (e.g. high definition, ultra-high definition, etc.) Thereafter, step S406 calculates a scaling factor which will then be applied to each value of the RAW image frame data. The scaling factor C(x,y) is calculated in accordance with Equation 2 which states:

$$C(x, y) = A(x, y) \frac{\max B(x)}{B(x)} \quad (2)$$

To generate the scaling factor, the algorithm determines, across all columns B(0)-B(9) the maximum brightness (or darkness) value, max B(x), and divides the maximum brightness by each wavelength value which changes the spacing between each pixel value. The original frame data is then multiplied by the result in order to generate the scaling factor which will be used when performing in-line spectral compensation on the original frame data. This is done on all the data within the frame so all B values in each column to get the proper distribution.

Turning back to FIG. 4, the original frame is then stored in a second buffer (312 in FIG. 3) in step S408 where each value in the original frame is compensated, in step S410, by multiplying the pixel values by the scaling factor calculated in step S406 in order to normalize the image and improve the field of view by making the darker areas in the frame brighter and making the brighter areas in the frame darker. The compensated frame generated in step S410 is then output for display in step S412. In another embodiment, the compensated frame may not be directly output but stored in a storage device for later viewing.

Figure 6A:
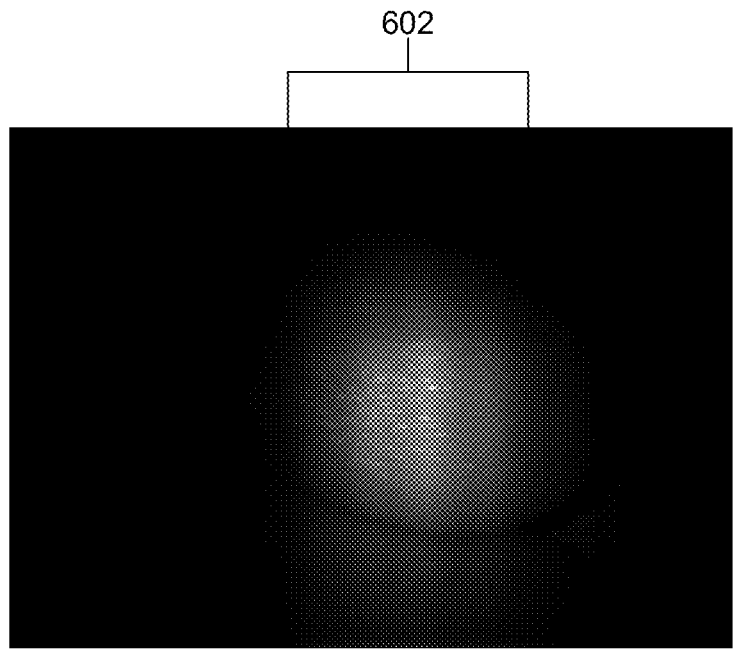
FIGS. 6A & B are exemplary images processed according to embodiment.
Figure 6B:
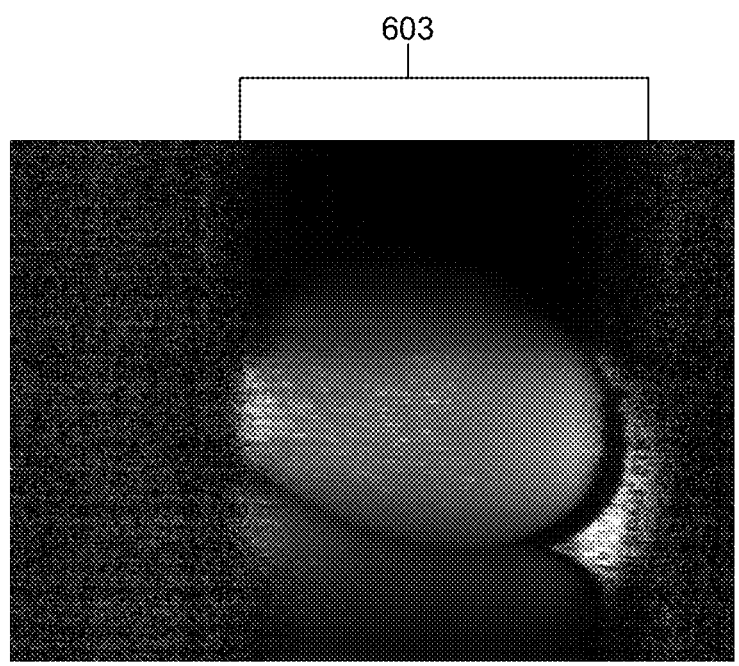

An exemplary result of the in-line spectrum compensation algorithm is depicted in FIGS. 6A and 6B. FIG. 6A illustrates a single image frame captured by the probe and generated as discussed above and has a field of view present between the bracket labeled 602. The in-line spectrum compensation processing is applied on a line scan over a defined scanning direction. As shown in FIGS. 6A and 6B, the vertical direction is scanning direction. The horizontal direction is the spectrally-encoded direction and the left and right edges of the entire frame correspond to 415 and 820 nm in design. The corrected image frame having the in-line spectrum compensation algorithm applied thereto is shown in FIG. 6B. By applying the calculated scaling factor to the data values in the original image frame, each data value in the frame is modified and a new corrected image frame is generated. The modification of the data values causes a display generator (or processor) to read and display the corrected image frame in a manner different than the original image frame. As shown in FIG. 6B, the display generator corrected image is transformed such that a wider field of view of a target area is visible as shown between brackets 603.

While the results of the algorithm described above with respect to FIGS. 3 and 4 yield superior results when generating corrected images as shown in FIG. 6B, other embodiments may yield similar results while improving the computational efficiency needed to process and correct image frames captured in high-frame rate applications such as video capture at a rate equal to or greater than 30 Hz. While the above described algorithm can also be applied in these higher frame rate applications, it becomes computationally more complex as the frame rate increases along with complexity of the image data being generated by the image processor. Another embodiment of the in-line spectrum compensation is depicted in FIG. 7.

Figure 7:
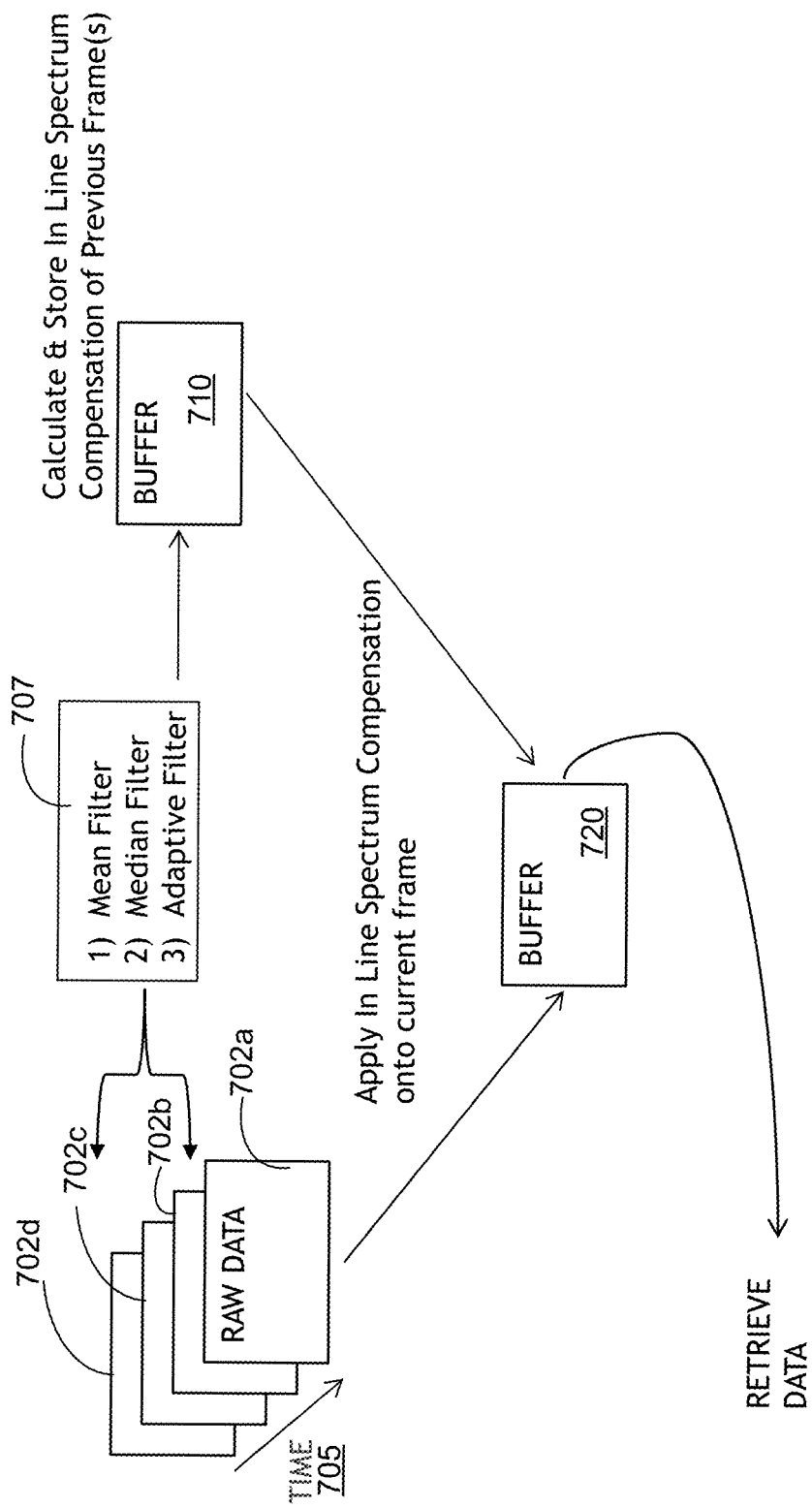
FIG. 7 shows schematic of another embodiment.

In FIG. 7, a series of image frames 702a-702d is shown. These image frames are captured and generated in a manner similar to those described with respect to FIG. 3, the description of which is incorporated herein by reference. In this embodiment, the algorithm separates the image frames in a current image 702a and a set of a predetermined number of previous image frames 702b-702d that were captured earlier in time than the current image frame 702a. In one exemplary embodiment, the predetermined number of previous image frames is three. However, any number of image frames may be determined to be included in the set of previous image frames. The previously captured image frames are stored in a first buffer 710 and a filtering algorithm is executed on the set of previous image frames in order to determine the scaling factor which will be applied to the current image frame 702a which includes raw image information captured by the probe 120. The current image frame 702a is stored in a second buffer 720 and awaits application of the scaling factor calculated by applying the filtering algorithm to the set of previous image frames stored in the first buffer. In one embodiment, the filtering algorithm is mean filtering algorithm. In another embodiment, the filtering algorithm is a median filtering algorithm. In a further embodiment, the filtering algorithm is an adaptive filtering algorithm. After application of the scaling factor to the current frame 702a in the second buffer 720, a corrected image frame is generated and is retrieved by a display generator 730 which outputs the corrected image for display.

It should be noted that the use of the terms first buffer and second buffer are intended for exemplary purposes and in order to clarify that different types of image data are stored in different areas of storage. In one embodiment, the first and second buffers are different buffers each having a predetermined size. In another embodiment, the first buffer and second buffer are discrete regions in a storage device or buffer each having a different input source.

Figure 8:
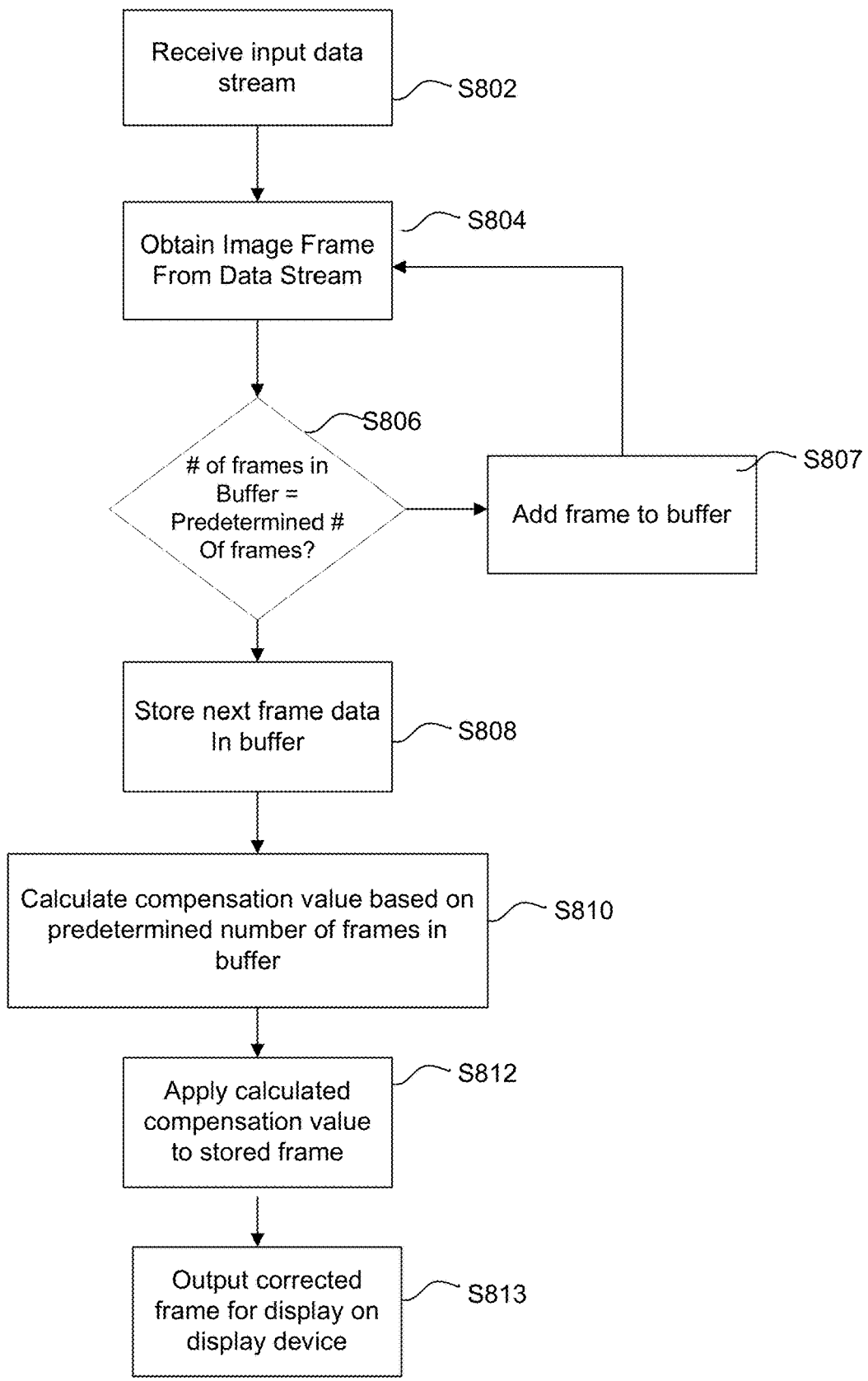
FIG. 8 is a flow diagram of an algorithm of an embodiment.

An exemplary algorithm associated for implementing the workflow described in FIG. 7 is provided in FIG. 8. In step S802, the image processor receives an input data stream comprised of individual image frames captured by the probe (120 in FIG. 1). The operation of this step is similar to that described above in step S402, the description of which is incorporated herein by reference. In step S804, an image frame is obtained from the input image stream received in step S802. In step S806, the algorithm determines whether a number of image frames stored in the first buffer equals a predetermined number of image frames. It is this step the begins the process of segmenting image frames from a data stream into the set of previously captured image frames used in calculating the scaling factor that will be applied to correct subsequent image frames. If the result of the determination in step S806 is negative (NO in S806), the algorithm adds the obtained image frame to the first buffer (710 in FIG. 7) in step S807 and reverts back to step S804 to obtain a next image frame from the input image data stream. If the result of the determination in step S806 is positive indicating that the first buffer has the predetermined number of previous image frames stored therein, the algorithm identifies the image frame as a current image frame and stores the raw, unprocessed image frame data in the second buffer (720 in FIG. 7). In step S810, the algorithm applies a filtering algorithm on the set of previous image frames stored in the first buffer to calculate a compensation value (e.g. scaling factor) that will be used in correcting the current image frame stored in the second buffer in step S812.

Referring back to step S810, the scaling factor calculated in step S810 is calculated in a similar manner as described above in FIG. 4 with certain exceptions which will be enumerated herein. Instead of performing an average of wavelength values for the single image frame, this embodiment applies a filtering algorithm over each of the frames in the set of previous frames stored in the first buffer. The filtering over a set of predetermined number of previous frames is computationally advantageous because, in such high frame rate applications, it is computationally wasteful to calculate on a per frame basis as the changes between individual frames are less pronounced. As such, the present embodiment advantageously uses a single calculation over the predetermined number of previous frames to obtain the scaling factor. This algorithm further reduces buffer bottlenecks and enables the compensation being applied to the current frame to occur in substantially real-time. Each value of the illumination spectrum B(x) in the spectral encoding direction is calculated over the number of predetermined frames stored in the first buffer. The original image data for each frame is provided as A(x,y) where x is the index for the frame in the spectrally encoded direction and y is the index for the scanning direction. This is similar to the graph shown in FIG. 5 and discussed above with respect to FIG. 4. However, an additional value representing an index of time of the frame sequence is represented by z. The algorithm applies a predetermined type of filter over the set of previously stored image frames. In one embodiment a mean filter is applied to the set of previously stored image frames in the first buffer. An exemplary mean filter is represented in Equation 3 below which states:

$$B(x) = \frac{\sum_{z=1}^{f} \sum_{k=1}^{n} A(x, k, z)}{n} \quad (3)$$

Each column representing a set of wavelengths is summed in the spectrally encoded direction which is further summed over the number of frames in the set of previous frames stored in the buffer. This sum over the number of previously stored frames is divided by the number of lines that make each frame (e.g. 1024) in order to normalize for each wavelength over the set of frames. Thereafter, step S406 calculates a scaling factor which will then be applied to each value of the RAW image frame data. The scaling factor C(x,y) is calculated in accordance with Equation 2 described above and which is repeated here and states:

$$C(x, y) = A(x, y) \frac{\max B(x)}{B(x)} \quad (2)$$

To generate the scaling factor, the algorithm determines, across all columns B(0)-B(9) and for each of the previously stored image frames, the maximum brightness (or darkness) value, max B(x), and divides the maximum brightness by each wavelength value which changes the spacing between each pixel value. The original frame data is then multiplied by the result in order to generate the scaling factor which will be used when performing in-line spectral compensation on the original frame data. This is done on all the data within the frame so all B values in each column to get the proper distribution.

The scaling factor calculated in step S810 is then applied to the current frame stored in the second buffer. The algorithm in step S812 multiplies the pixel values by the scaling factor calculated in step S810 in order to normalize the current image frame and improve the field of view by making the darker areas in the frame brighter and making the brighter areas in the frame darker. The compensated frame generated in step S812 is then output for display in step S813. In another embodiment, the compensated frame may not be directly output but stored in a storage device for later viewing. Optionally, data representing the compensated frame may also be fed back into the first buffer which expels the image frame stored at the earliest point in time thereby allowing scaling factors to be applied to subsequent image frames to be calculated using previously corrected image frames.

In another embodiment, the filtering algorithm employed in step S810 to generate the scaling factor is a median filtering algorithm. In this embodiment, to apply a median filter the algorithm in step S810 creates a dimensional mask that represents the previous illumination spectra for a given spectrally encoded direction. An exemplary dimensional mask R representing the current and three previous illumination spectra for a given spectrally encoded direction may be shown as 4×1 dimensional mask, where each of the four (4) boxes (which may be vertically stacked or structured to operate as the dimensional mask R) in the 4×1 dimensional mask R has the following values, respectively: Bxz1, Bxz2, Bxz3, Bxz4. The median filter calculates the nearest neighbor approximation as B(new) by obtaining a median value of the dimensional mask R and multiplying that by a sum of wavelength values at each line divided by the number of lines n of the current frame as shown in Equation 4.

$$B(\text{new}) = \text{med}\{R\} \Sigma_{k=1}^{n} A(x,k) \quad (4)$$

Figure 9A:
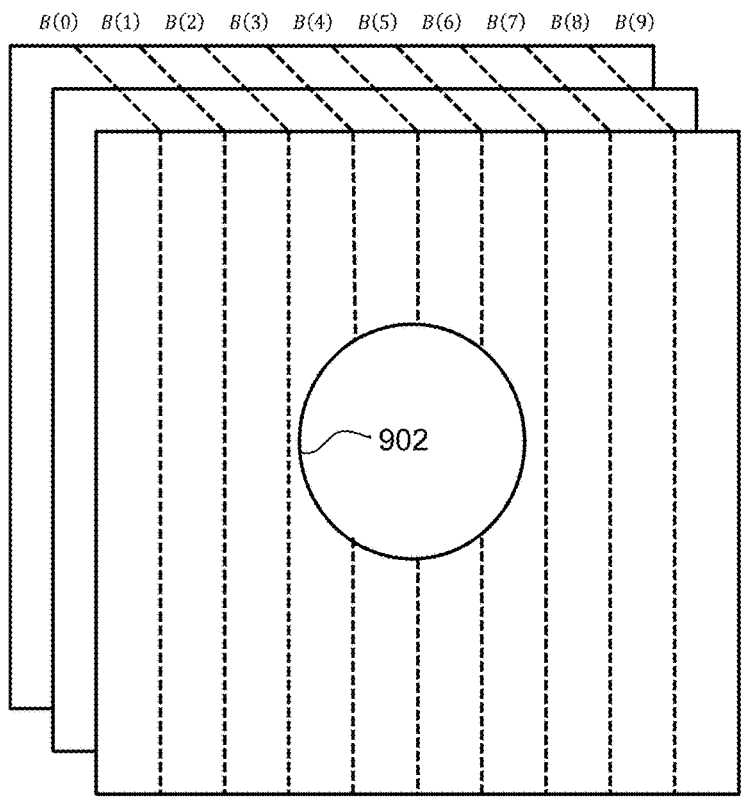
FIGS. 9A & 9B illustrate graphs of an embodiment.
Figure 9B:
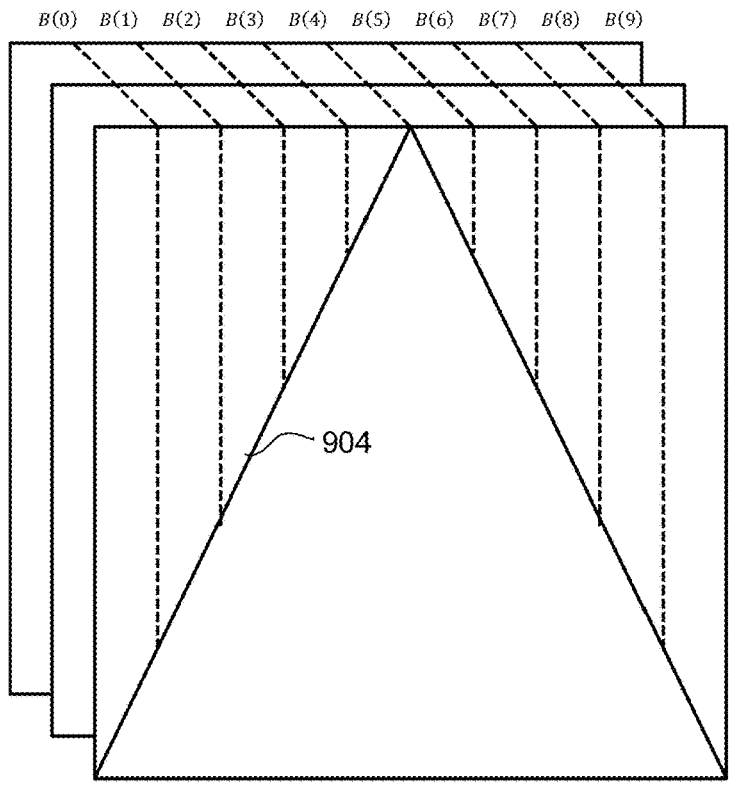

In a further embodiment, the filtering algorithm employed in step S810 is an adaptive filtering algorithm. In this embodiment, the adaptive filtering algorithm presumes that there is minimal change to the background in a series of image frames and instead only performs the calculation on a predetermined area in an image frame determined to be the target area. This is illustrated in FIGS. 9A and 9B which each illustrate the set of previously stored image frames in the first buffer where each frame has a target object shown therein. In FIG. 9A, the target object is within a boundary defined by circular line 902 and the target object in FIG. 9B is within a boundary defined by triangular line 904. Thus, the calculations to determine the scaling factor are determined using only the data within the respective boundaries 902 and 904. Further, in when applying calculated scaling factor in step S812, the algorithm only applies it to image data within a similarly defined boundary in the current image frame stored in the second buffer. An exemplary manner in which the adaptive filtering may be applied over the set of previous frames stored in the first buffer is as follows. The algorithm makes use of an input signal A(x,y) representing the original image frame as discussed above, output B(x,n), and assumes a known desired response D(x,n), where n is time. A difference signal S(n) is given as S(x,n)=D(n)−B(x,n). The adaptive filter inputs the difference signal into a procedure which adapts the parameter of the filter from time n to time (n+1) in a deterministic manner resulting in the parameters being shifted to decrease S(n) over time. In a finite parametric system, the coefficient vector V(n) is defined as $V(n)=[v_0(n)v_1(n)\ldots v_{L-1}(n)]$, where $\{v_i(n)\}, 0 \leq i \leq L-1$ are the L parameters of the system at time n.

Figure 10:
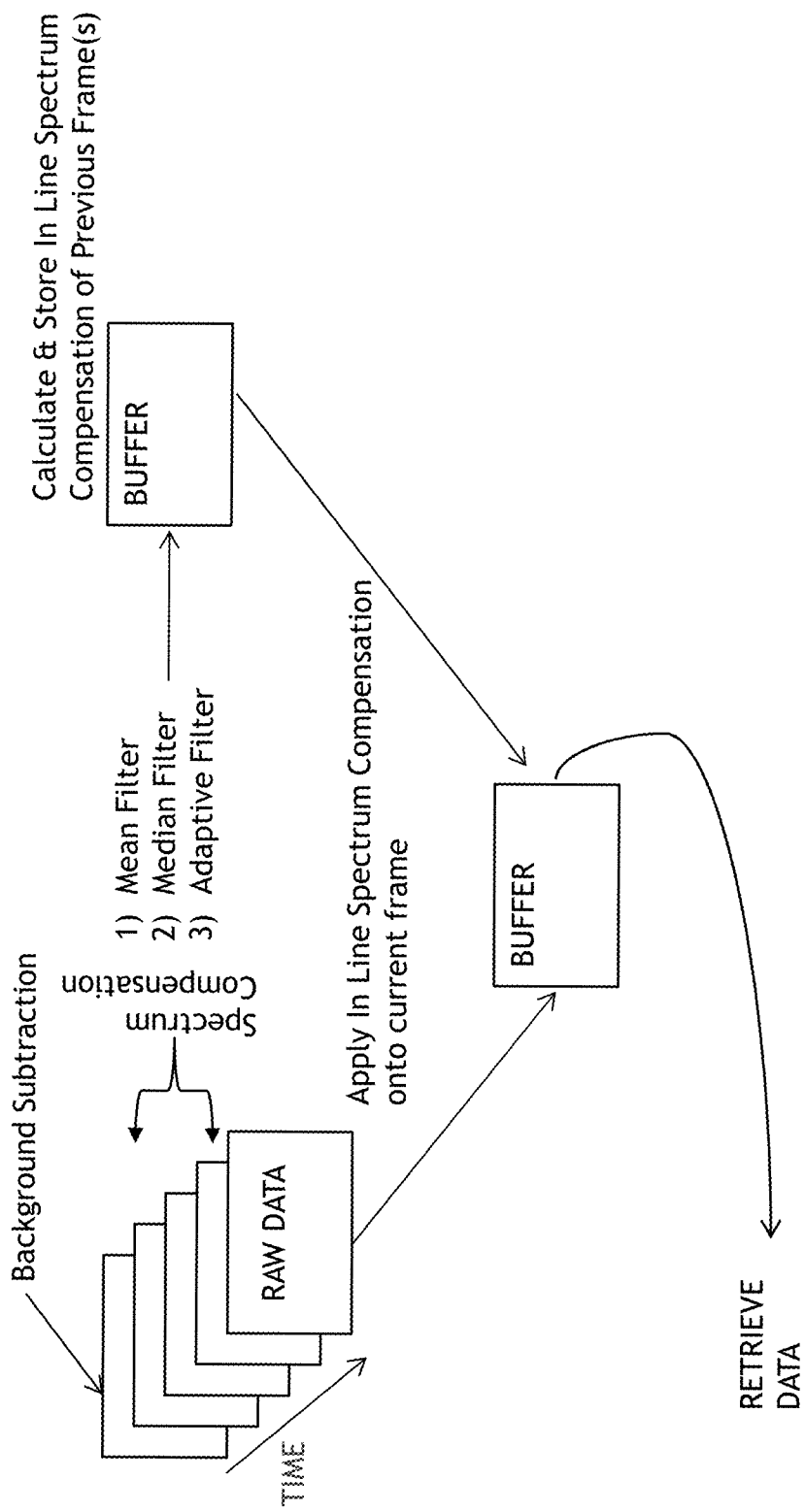
FIG. 10 shows schematic of another embodiment.

FIG. 10 illustrates a further embodiment that is provides an additional feature to the workflow discussed above in FIGS. 7 & 8. In the embodiment shown in FIG. 10, prior to storing the previously received image frames into the first buffer a background correction algorithm which subtracts pixel values between the target frame and a background frame. The pixel subtraction would operate on the previously received frames stored in the first buffer and functions in a manner to remove some of the high saturation noise from the respective current image frame being corrected.

Figure 11:
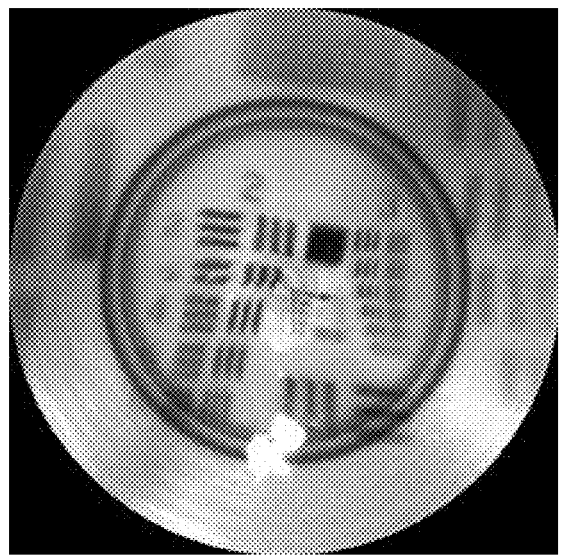
FIG. 11 shows an image to be processed by an embodiment.

In addition to the in-line compensation algorithms outlined above, further pre-processing algorithms may be applied to each frame in order to remove certain image artifacts prior to performing the in-line compensation algorithm discussed above. A first type of artifact may present itself as a series of black rings within the image as shown in FIG. 11. This may be caused when the images captured by the probe are on a surface having high specular reflection associated therewith due to the rotational manner in which the probe captures these images. The artifact presents itself as a dark ring with intense black values. Another type of artifact presents itself as a group of pixels having an intense white value. Because these pixel values are at each end of the intensity spectrum, it would be advantageous to correct these images to remove or otherwise exclude the pixels in the image frame where these artifacts exist.

Figure 12:
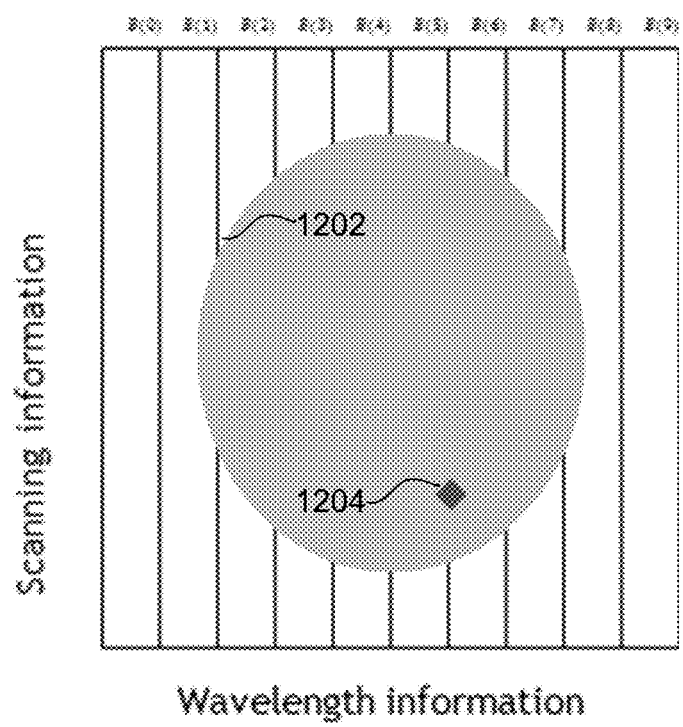
FIG. 12 is a graph representing the image of FIG. 11.

In a first pre-processing step, one or more pixels are identified as being artifacts by analyzing the pixel values of the respective image frame. In one embodiment, the identification of the these values indicative of an artifact may be performed by obtaining a histogram of the image frame. Continuing with the sample image in FIG. 11, a representative histogram of that image is shown in FIG. 12. In FIG. 12, the artifact representative of the black circle having intense black value is shown as the border of the circle 1202 while the artifact indicative of the intense white pixels is shown by the diamond 1204 within the circle 1202. Table 1, shown below, show the values in the spectrally encoded direction for an image having five colors B(0)-B(4).

TABLE 1

| B(0) | B(1) | B(2) | B(3) | B(4) |
|---|---|---|---|---|
| 1 | 0 | 1 | 0 | 1 |
| 1 | 5 | 1 | 10 | 1 |
| 1 | 10 | 1 | 10 | 1 |
| 1 | 5 | 1 | 220 | 1 |
| 1 | 5 | 1 | 10 | 1 |

In the scanning direction of the image represented by Table 1, we have one area with "very high" intensities as shown as the diamond 1204 in FIG. 12. This corresponds to the bright spots that appear in FIG. 11. Because the intensity in this area is so strong, if the in-line compensation algorithm discussed above were to be executed on this image, the sum intensity B(x) will become abnormally larger. Table 1 shows pixel grayscale values for the exemplary image. It is clear that the B(0)=1, B(1)=5, B(2)=1, B(3)=50, B(4)=1. Thus Max(B(x))=50. If one were to perform the in-line compensation algorithm discussed above, the corrected image could be represented by the Table 2.

TABLE 2

| B(0) | B(1) | B(2) | B(3) | B(4) |
|---|---|---|---|---|
| 50 | 0 | 50 | 0 | 50 |
| 50 | 50 | 50 | 10 | 50 |
| 50 | 100 | 50 | 10 | 50 |
| 50 | 50 | 50 | 220 | 50 |
| 50 | 50 | 50 | 10 | 50 |

Because of the large number in B(3), this column is largely not changed but all other columns benefits from the scaling factor $$\frac{\max B(x)}{B(x)}.$$

In other words, we observe the dark ring as shown in FIG. 11. The preprocessing algorithm described herein identifies areas within a respective image frame that would present itself with high numbers in tables similar to Table 1. The high numbers refers to an extreme intensity value on the intensity spectrum for each pixel.

In order to identify pixels representative of a type of artifact within the image frame, in one embodiment, the preprocessing algorithm obtains a histogram for the entire image within an image frame. Thereafter, based on histogram analysis, the algorithm identifies pixels that have an intensity value higher than a predetermined intensity threshold. In certain embodiments, the predetermined intensity threshold may be an arbitrary percent representing pixels having an intensity value within the top intensity values within the image frame. For example, pixels having an intensity value within the top one percent of intensity values across the image may be identified as artifacts. In another embodiment, instead of setting an arbitrary intensity value, the preprocessing algorithm may apply one or functions to fit the histogram to identify pixels with a high intensity value. On manner of doing this is to take a Gaussian distribution of the histogram to identify the pixels having a sufficient intensity value to be deemed representative of artifacts. In another embodiment, the preprocessing algorithm calculates all the moments of the histogram distribution including average, standard deviation, skewness, etc. and any pixel having a value larger than predetermined measure (e.g. average+2 standard deviations) is set as a pixel that is part of an artifact. This threshold is provided for exemplary purposes only and is advantageous because, for normal distributions, the values that are two standard deviations from the mean account for substantially 95% of the values in the entire set.

In another embodiment that identifies the pixels in an image frame that are indicative of artifacts, the preprocessing algorithm executes a binary segmentation algorithm which segments the image frame based on a binary threshold. The algorithm obtains a baseline maximum brightness value for the entire image and any pixel within the image frame that has a brightness value greater than the baseline threshold is identified and included in a binary mask of the image whereby the mask covers pixels indicative of an artifact.

After identifying pixels that are considered artifacts, these pixels can be mapped and excluded when performing the in-line spectrum compensation algorithm discussed above. Alternatively, an average pixel value for all pixels within the image frame can be obtained and applied to pixels that are identified as being indicative of artifacts in the image frame.

Figures 13A, 13B:
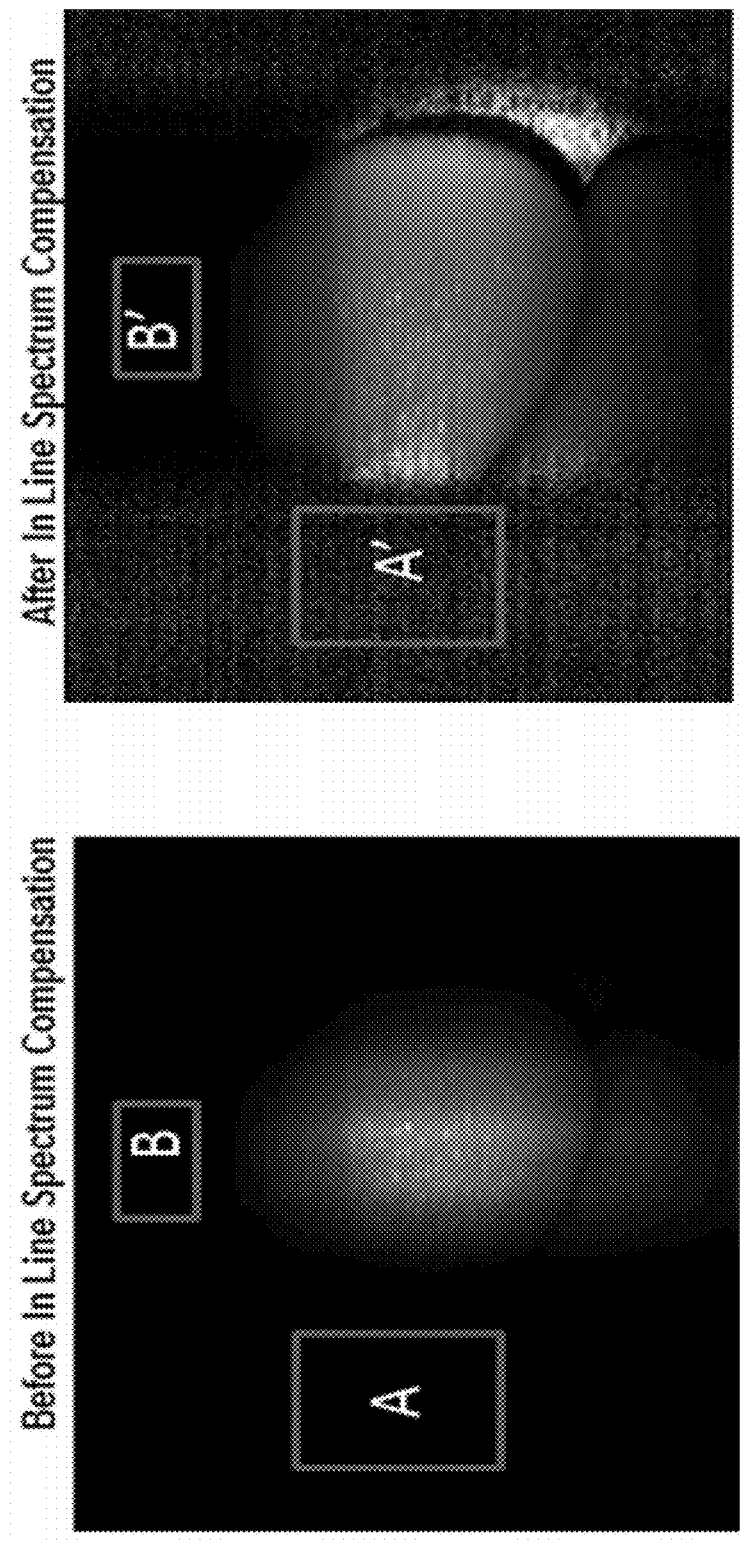
FIGS. 13A & 13B are exemplary images processed according to an embodiment.

In another embodiment, the preprocessing algorithm can selectively identify regions of the image frame which have low or no signal and advantageously exclude them from having the in-line spectrum compensation algorithm being applied thereto. For example, FIG. 13A illustrates an image frame similar to that shown in FIG. 6A. However, in FIG. 13A, Regions A and B represent regions that will likely be improved after having the in-line compensation algorithm applied thereto. This is confirmed when looking to FIG. 13B which illustrates the same image frame after being corrected via the in-line spectrum compensation algorithm discussed above. It is important to note that the signal level in area A' has been boosted but all that has been introduced is noise. Thus, the preprocessing algorithm can exclude the pixels in the area from being subject to the compensation algorithm.

In this embodiment, the preprocessing algorithm improves the selection area by implementing a kernel selection using a window of a predetermined size (e.g. 7×7 or 5×5 pixel window) that moves across the image frame in order to improve the signal to noise ratio. In one embodiment, the algorithm may employ a kernel smoothing algorithm using the defined window to improve the signal to noise ratio.

Figure 14:
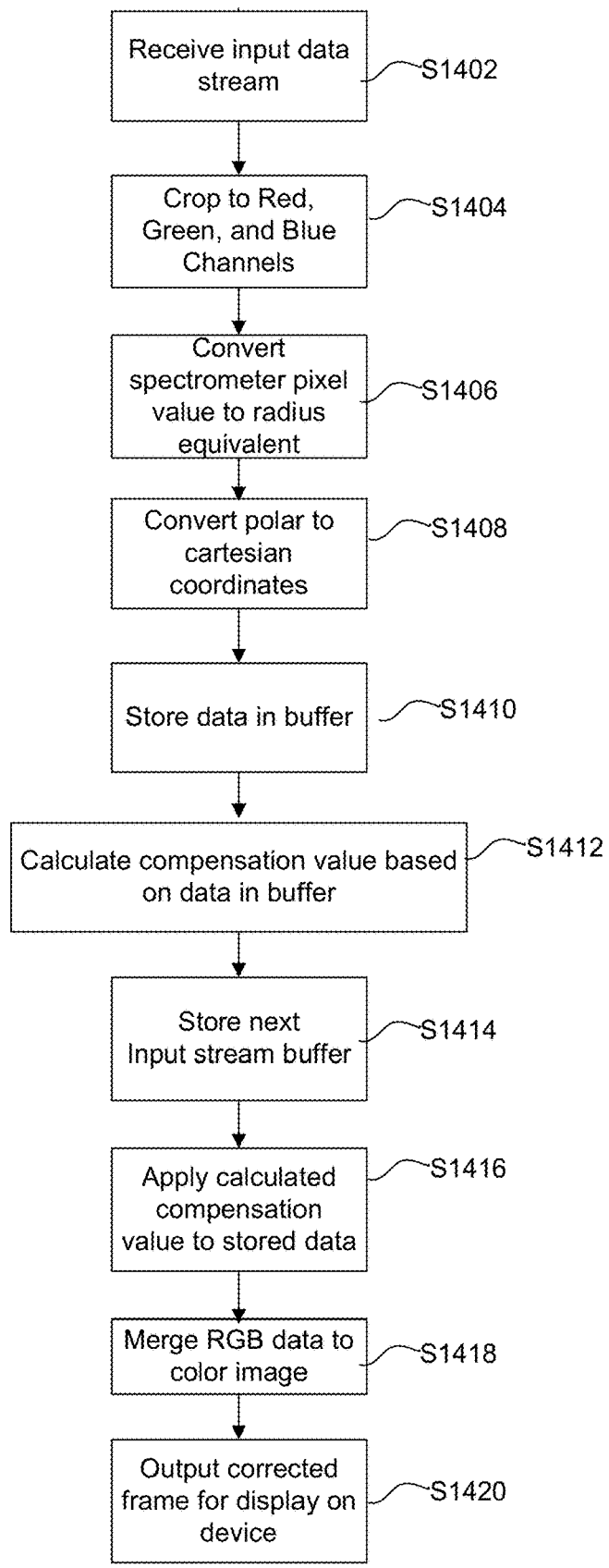
FIG. 14 is a flow diagram of an algorithm of an embodiment.

FIG. 14 illustrates an algorithm for in-line spectrum correction for images captured by an image capture apparatus whereby the captured image frames each have a plurality of image channels each corresponding to a different spectrum. In one embodiment, the algorithm described with respect to FIG. 14 may be used to correct spectrum in image frames captured having three color channels (e.g. a red channel, a green channel and a blue channel). This algorithm may be implemented by image processor (150 in FIGS. 1 and 2) on image data captured by the probe 120 and processed by spectrometer 142. Further, this algorithm may be integrated into the image processing workflow described above with respect to at least FIGS. 3 and 7. However, not specifically mentioning other of the figures described herein is not intended to mean that the algorithm of FIG. 14 is incompatible in any way and persons skilled in the art would understand the manner to integrate any and all algorithms described herein.

In FIG. 14, raw image data is first acquired on a frame by frame basis in step S1402 as 16 bit data having a predetermined data structure. In one embodiment, the predetermined data structure is a dimensional array where a first dimension represents a number of scanning lines in the frame, a second dimension represents a pixel resolution and the third dimension represents a number of input streams. In one embodiment, the predetermined array size has a data structure of 1000×2048×2. The predetermined array size set forth above is described for purposes of example only and is not intended to be limited to an array of that size. In one embodiment, one of the respective plurality of channels is acquired separately from the other of the plurality of channels. For example, the blue channel may be acquired separately from the red and green channels. However, it should be understood that this is merely exemplary and all of the channels can be acquired collectively or individually. Thus, in the predetermined data structure, the number of input streams corresponds to a number of separate channels acquired and processed by a spectrometer. The raw image data acquired in step S1402 represents a frame represented as the number of scanning lines by the spectrometer wavelength represented as pixels. In step 1404, the RAW data frame is cropped (or otherwise segmented) into the red, green, and blue regions. In step S1406, the combination of the spectrometer data that generates data values reflecting wavelengths sensed by the one or more sensors of the probe, as well as information about the color wavelengths, and the mechanical properties of the SEE probe, are used to represent the data as polar coordinates (r, 0) in order to transition the image data from the time and pixel information at which it was captured into an desired output endoscopic image view. In other words, the algorithm uses the time and pixel information provided by the spectrometer and the parameters of the SEE probe, such as the groove density of its grating (as well as other parameters), in order to construct an endoscopic polar view representation of the image characterized by a radial coordinate and a polar angle with respect to the probe. At this point, the first dimension represents the number of scanning lines, the second dimension is the radius of the field of view in polar space in pixels. This is engineering user defined and can be dynamic whereby the third dimension in the predetermined data structure specifies which information is attributed to which channel. For example, the acquired image data frame is two dimensional but the correction processing needs to be propagated forward on per channel basis based on the third dimension which represents the number of channels. In step S1408, the image processor converts polar coordinates into Cartesian coordinate space (x,y) and normalizes all three channels to have the same dimensions wherein the first two dimensions represent the x and y coordinates and the third dimension represents the number of channels. The data generated in step S1408 is stored into a buffer in step S1410 and the spectrum compensation is calculated for the data stored in the buffer in step S1412. A further (or next) input data stream is stored in another buffer in step S1414. In step S1416, the calculated compensation value from S1412 is applied to the further input data stream stored, in Step S1414, in the other buffer once the input data stream stored in S1414 it has been translated into Cartesian space as discussed above. After spectrum correction, each of the individual image channels (RGB data channels) on which this process has been performed is merged in step S1418 and output corrected frame for display on a display device in step S1420.

Figure 15:
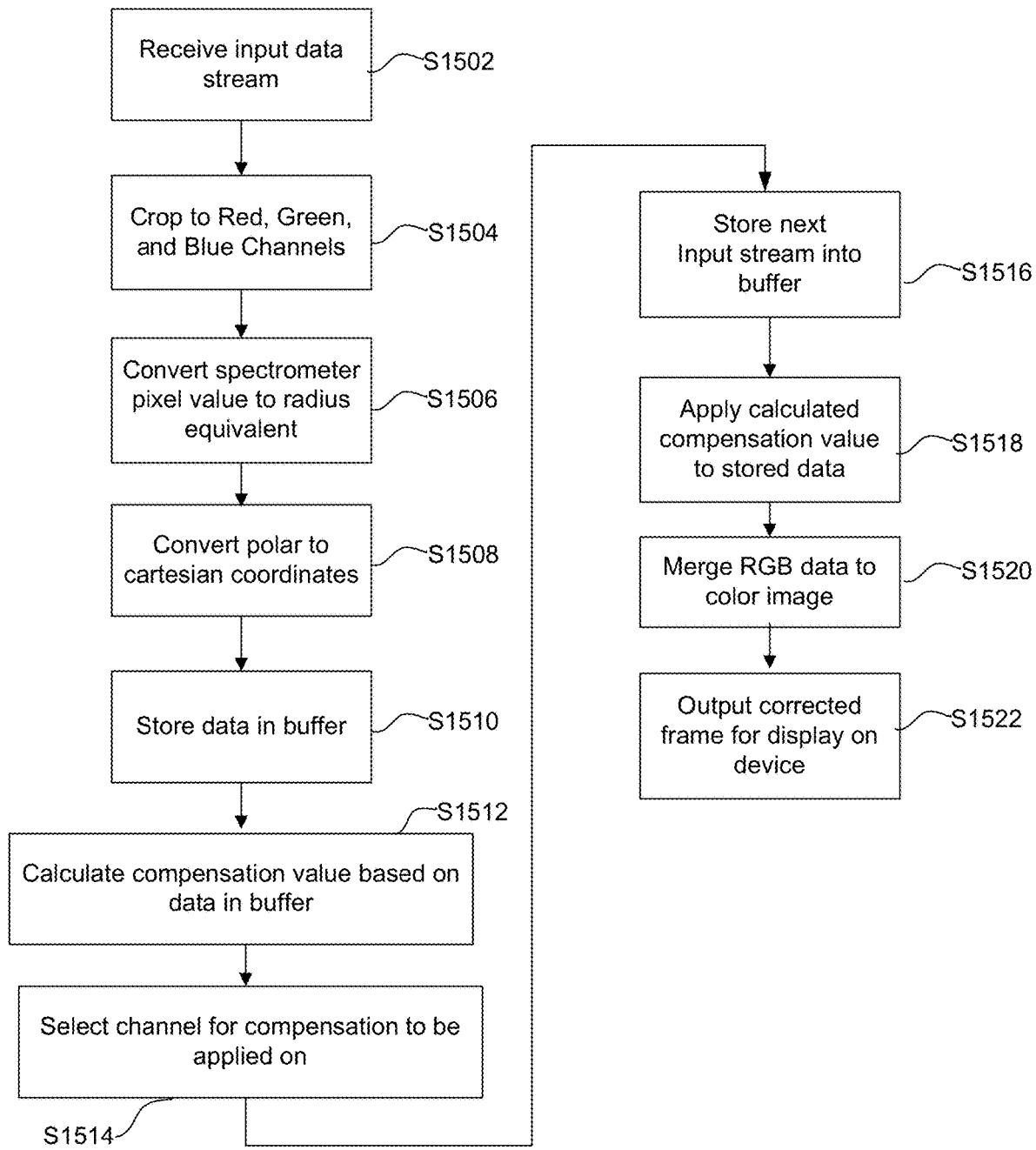
FIG. 15 is a flow diagram of an algorithm of an embodiment.

FIG. 15 illustrates an algorithm for in-line spectrum correction for images captured by an image capture apparatus whereby the captured image frames each have a plurality of image channels where at least one of the plurality of channels is of a first type and at least one other of the plurality of channels is a second type different from the first type. This may include a partial color image. In one embodiment, the algorithm described with respect to FIG. 15 may be used to correct spectrum in image frames captured having at least one color channel and at least one non-color channel). This algorithm may be implemented by image processor (150 in FIGS. 1 and 2) on image data captured by the probe 120 and processed by spectrometer 142. Further, this algorithm may be integrated into the image processing workflow described above with respect to at least FIGS. 3 and 7. However, not specifically mentioning other of the figures described herein is not intended to mean that the algorithm of FIG. 15 is incompatible in any way and persons skilled in the art would understand the manner to integrate any and all algorithms described herein.

FIG. 15 includes certain similar features as those described above with respect to FIG. 14. For examples steps S1502-S1512 correspond to steps S1402-S1412, the description of which is hereby incorporated by reference and need not be repeated here. Subsequent to Step S1412, the algorithm in step S1514, the individual channel(s) can be manually selected for spectrum compensation in step S1516. The channels not selected will have not have spectrum compensation applied. In another embodiment, the channels may be selected dynamically according to one of an environmental characteristic or a target-specific characteristic such that compensation applied can be dynamically changed and applied to different channels in a disproportionate manner. In other embodiments, channels that are not selected (either manually or dynamically) may have a predetermined correction amount applied thereto based on, for example, if a determination is made that the compensation needed is stable over a period of time. After the selection of channels to which correction will be applied, the algorithm in FIG. 15 continues in steps S1516-S1522 which correspond steps S1414-S1420 of FIG. 14 which are hereby incorporated by reference and need not be repeated.

In referring to the description, specific details are set forth in order to provide a thorough understanding of the examples disclosed. In other instances, well-known methods, procedures, components, and circuits have not been described in detail as not to unnecessarily lengthen the present disclosure.

It should be understood that if an element or part is referred herein as being "on", "against", "connected to", or "coupled to" another element or part, then it may be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90° or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

We claim:
1. An image processing apparatus comprising:
one or more processors; and
a memory storing instructions, which when executed by the one or more processors controls the one or more processors to:
receive image stream data captured by an image capturing apparatus;
store, in memory, a current image frame from the received image stream data;
store, in memory, a previously received image frame from the received image stream data, the previously received image frame having been received at a time earlier than the current image data frame;
calculate, using the previously received image frame stored in memory, a compensation value representing an illumination spectrum of the previously stored image frame;
perform image correction on the current image frame using the calculated compensation value; and
output the corrected current image frame for display on a display device, wherein:
image correction on the current image frame is performed using a scaling factor determined based on a maximum brightness value of the previously stored image frame data and for each pixel value, dividing the maximum brightness value by a brightness value at each pixel; and
each pixel of the current image frame data is transformed by the scaling factor to generate the corrected current image frame data.

2. The image processing apparatus of claim 1, wherein the compensation value is calculated by binning and averaging pixel values along a spectral coding direction of the previously received image frame.

3. The image processing apparatus of claim 2, wherein the compensation value is calculated by, for each wavelength captured in the previously stored image frame, summing values representative of the wavelength in the spectrally encoded direction and dividing the summed values by a total number of lines of the previously stored image frame.

4. The image processing apparatus of claim 1, wherein image correction on the current image frame is performed by multiplying each pixel value by the calculated compensation value to obtain a corrected pixel value, and
generating the corrected image data by storing the corrected pixel values in memory.

5. The image processing apparatus of claim 1, wherein image correction being performed using the compensation value increases a brightness of pixels having a predetermined darkness level and increases or decreases a brightness of pixels having a predetermined brightness level.

6. The image processing apparatus of claim 1, wherein the current image frame is stored in a first memory device; and
the previously received image frame is stored in a second different memory device.

7. An image processing method comprising:
receiving image stream data captured by an image capturing apparatus;
storing, in memory, a current image frame from the received image stream data;
storing, in memory, a previously received image frame from the received image stream data, the previously received image frame having been received at a time earlier than the current image frame;
calculating, using all of the previously received image frame data stored in memory, a compensation value representing an illumination spectrum of the previously stored image frame;
performing image correction on the current image frame data using the calculated compensation value; and
outputting the corrected current image frame for display on a display device, wherein:
correcting the current image frame is performed using a scaling factor determined based on a maximum brightness value of the previously stored image frame data and for each pixel value, dividing the maximum brightness value by a brightness value at each pixel; and
the method further includes transforming each pixel of the current image frame data by the scaling factor to generate the corrected current image frame data.

8. The image processing method of claim 7, further comprising
calculating the compensation value by binning and averaging pixel values along a spectral coding direction of the previously received image frame.

9. The image processing method of claim 8, wherein for each wavelength captured in the previously stored image frame, calculating the compensation value by summing values representative of the wavelength in the spectrally encoded direction and dividing the summed values by a total number of lines of the previously stored image frame.

10. The image processing method of claim 7, wherein correcting the current image frame includes
multiplying each pixel value by the calculated compensation value to obtain a corrected pixel value, and
generating the corrected image data by storing the corrected pixel values in memory.

11. The image processing method of claim 7, wherein image correction being performed using the compensation value increases a brightness of pixels having a predetermined darkness level and increases or decreases a brightness of pixels having a predetermined brightness level.

12. The image processing method of claim 7, wherein the current image frame data is stored in a first memory device; and
the previously received image frame data is stored in a second different memory device.

13. An image processing apparatus comprising:
one or more processors; and
a memory storing instructions, which when executed by the one or more processors controls the one or more processors to
receive image stream data captured by an image capturing apparatus;
store, in memory, a current image frame from the received image stream data;
store, in memory, a predetermined number of previously received image frames from the received image stream data, each of the predetermined number of previously received image frames having been received at a time earlier than the current image data frame;
filter the predetermined number of previously received image frame data stored in memory to generate a scaling factor for normalizing pixel brightness, the scaling factor determined based on at least a maximum brightness value of the previously stored image frame data and for each wavelength value, dividing the maximum brightness value by a brightness value by a brightness value at each wavelength in a spectrally encoded direction;

perform image correction on the current image frame data using the scaling factor; and output the corrected current image frame for display on a display device.

14. The image processing apparatus of claim 13, wherein the scaling factor is calculated using the predetermined number of previously received image frames by binning and averaging pixel values along the spectral coding direction in each of the predetermined number of previously received image frames; and averaging, as a group, the average pixel values for each frame.

15. The image processing apparatus of claim 13, wherein the filtering performed on the predetermined number of previously stored image frames is one of (a) a mean filter; (b) a median filter; and (c) an adaptive filter.

16. The image processing apparatus of claim 13, wherein image correction on the current image frame is performed by multiplying each pixel value by the scaling factor to obtain a corrected pixel value, and generating the corrected image data by storing the corrected pixel values in memory.

17. The image processing apparatus of claim 13 wherein the scaling factor determined is based on a maximum brightness value present in any of the predetermined number of previously stored image frames and for each wavelength value, dividing the maximum brightness value by a brightness value of at each wavelength in the spectrally encoded direction; and each pixel of the current image frame data is transformed by the scaling factor to generate the corrected current image frame data.

18. The image processing apparatus of claim 13, wherein the current image frame is stored in a first memory device; and the previously received image frame is stored in a second different memory device.

19. The image processing apparatus of claim 13, wherein execution of the stored instructions controls the one or more processors to identify at least one region in the predetermined number of previously received image frames as a target region to generate the scaling factor only for pixels within the identified target region; and perform image correction on pixels in a region in the current image frame corresponding to the target region.

20. The image processing apparatus of claim 13, wherein execution of the stored instructions controls the one or more processors to identify pixels in one or more of the predetermined number of previously received image frames as background pixels; and perform image correction on pixels in the current image frame corresponding to pixels identified as background pixels.

21. The image processing apparatus of claim 13, wherein execution of the stored instructions controls the one or more processors to identify one or more pixels in a respective one of the predetermined number of previously received image frames as being indicative of an artifact; and exclude, from the filtering to generate the scaling factor, the identified one or more pixels.

22. The image processing apparatus of claim 21, wherein the one or more pixels are identified as an artifact by generating a histogram of the respective one of the predetermined number of previously received image frames and selecting pixel values that exceed a predetermined intensity threshold.

23. The image processing apparatus of claim 21, wherein the one or more pixels are identified as an artifact by performing binary segmentation on the respective one of the predetermined number of previously received image frames to identify pixels having a brightness value that exceeds a predetermined brightness threshold;

generating a map of the identified pixels; and excluding the mapped pixels from the filtering.

24. The image processing apparatus of claim 13, wherein execution of the stored instructions controls the one or more processors to generate a window having a predetermined pixel width and predetermined pixel height at an origin point on a respective one of the predetermined number of previously received image frames;

move the generated window over the respective one of the predetermined number of previously received image frames; and perform kernel smoothing on pixels within the generated window as the generated window is moved to improve signal to noise ratio in the respective one of the predetermined number of previously received image frames.

25. The image processing apparatus of claim 13, wherein the image capture device that captures the image stream data is a spectrally encoded endoscope.

26. The image processing apparatus of claim 13, wherein the image data stream is captured at a rate of at least 30 frames per second.

27. An image processing method comprising:

receiving image stream data captured by an image capturing apparatus;

storing, in memory, a current image frame from the received image stream data;

storing, in memory, a predetermined number of previously received image frames from the received image stream data, each of the predetermined number of previously received image frames having been received at a time earlier than the current image data frame;

filtering the predetermined number of previously received image frame data stored in memory to generate a scaling factor for normalizing pixel brightness, the scaling factor determined based on at least a maximum brightness value of the previously stored image frame data and for each wavelength value, dividing the maximum brightness value by a brightness value by a brightness value at each wavelength in a spectrally encoded direction;

performing image correction on the current image frame data using the scaling factor; and outputting the corrected current image frame for display on a display device.

28. The image processing method of claim 27, wherein the scaling factor is calculated using the predetermined number of previously received image frames by binning and averaging pixel values along a spectral coding direction in each of the predetermined number of previously received image frames; and averaging, as a group, the average pixel values for each frame.

29. The image processing method of claim 28, wherein the filtering performed on the predetermined number of previously stored image frames is one of (a) a mean filter; (b) a median filter; and (c) an adaptive filter.

30. The image processing method of claim 27, further comprising
performing image correction on the current image frame by multiplying each pixel value by the scaling factor to obtain a corrected pixel value, and
generating the corrected image data by storing the corrected pixel values in memory.

31. The image processing method of claim 27, further comprising
determining the scaling factor based on a maximum brightness value present in any of the predetermined number of previously stored image frames and, for each wavelength value, dividing the maximum brightness value by a brightness value of at each wavelength in the spectrally encoded direction; and
transforming each pixel of the current image frame data by the scaling factor to generate the corrected current image frame data.

32. The image processing method of claim 27, wherein the current image frame is stored in a first memory device; and
the previously received image frame is stored in a second different memory device.

33. The image processing method of claim 27, further comprising
identifying at least one region in the predetermined number of previously received image frames as a target region to generate the scaling factor only for pixels within the identified target region; and
performing image correction on pixels in a region in the current image frame corresponding to the target region.

34. The image processing method of claim 27, further comprising
identifying pixels in one or more of the predetermined number of previously received image frames as background pixels; and
performing image correction on pixels in the current image frame corresponding to pixels identified as background pixels.

35. The image processing method of claim 27, further comprising
identifying one or more pixels in a respective one of the predetermined number of previously received image frames as being indicative of an artifact; and
excluding, from the filtering to generate the scaling factor, the identified one or more pixels.

36. The image processing apparatus of claim 35, wherein the one or more pixels are identified as an artifact by
generating a histogram of the respective one of the predetermined number of previously received image frames and selecting pixel values that exceed a predetermined intensity threshold.

37. The image processing apparatus of claim 35, wherein the one or more pixels are identified as an artifact by
performing binary segmentation on the respective one of the predetermined number of previously received image frames to identify pixels having a brightness value that exceeds a predetermined brightness threshold;
generating a map of the identified pixels; and
excluding the mapped pixels from the filtering.

38. The image processing method of claim 27, further comprising
generating a window having a predetermined pixel width and predetermined pixel height at an origin point on a respective one of the predetermined number of previously received image frames;
moving the generated window over the respective one of the predetermined number of previously received image frames; and
performing kernel smoothing on pixels within the generated window as the generated window is moved to improve signal to noise ratio in the respective one of the predetermined number of previously received image frames.

39. The image processing method of claim 27, wherein the image capture device that captures the image stream data is a spectrally encoded endoscope.

40. The image processing method of claim 27, wherein the image data stream is captured at a rate of at least 30 frames per second.

* * * * *